United States Patent
Yokosaki et al.

(10) Patent No.: US 10,822,418 B2
(45) Date of Patent: Nov. 3, 2020

(54) FIBROSIS SUPPRESSION BY INHIBITING INTEGRIN α-8 β-1 FUNCTION

(71) Applicant: Hiroshima University, Hiroshima (JP)

(72) Inventors: Yasuyuki Yokosaki, Hiroshima (JP); Norihisa Nishimichi, Hiroshima (JP)

(73) Assignee: Hiroshima University, Hiroshima (JP)

( * ) Notice: Subject to any disclaimer, the term of this patent is extended or adjusted under 35 U.S.C. 154(b) by 0 days.

(21) Appl. No.: 14/388,134

(22) PCT Filed: Mar. 28, 2013

(86) PCT No.: PCT/JP2013/059368
§ 371 (c)(1),
(2) Date: Sep. 25, 2014

(87) PCT Pub. No.: WO2013/147076
PCT Pub. Date: Oct. 3, 2013

(65) Prior Publication Data
US 2015/0064187 A1    Mar. 5, 2015

(30) Foreign Application Priority Data

Mar. 28, 2012 (JP) ................. 2012-075147

(51) Int. Cl.
| | |
|---|---|
| *A61K 39/395* | (2006.01) |
| *A61K 39/00* | (2006.01) |
| *C07K 16/28* | (2006.01) |
| *A61K 45/06* | (2006.01) |

(52) U.S. Cl.
CPC .......... *C07K 16/2842* (2013.01); *A61K 45/06* (2013.01); *C07K 16/2839* (2013.01); *A61K 2039/505* (2013.01); *C07K 2317/23* (2013.01); *C07K 2317/33* (2013.01); *C07K 2317/34* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 5,567,440 A | * | 10/1996 | Hubbell ................ | A61K 9/5031 424/484 |
| 2002/0182213 A1 | | 12/2002 | Gotwals et al. | |
| 2004/0037827 A1 | | 2/2004 | Gotwals et al. | |
| 2005/0281818 A1 | | 12/2005 | Gotwals et al. | |
| 2007/0048321 A1 | | 3/2007 | Gotwals et al. | |
| 2012/0237530 A1 | | 9/2012 | Matsuda et al. | |

FOREIGN PATENT DOCUMENTS

| | | |
|---|---|---|
| CA | 2778401 A1 | 4/2011 |
| JP | 2002-542300 A | 12/2002 |
| WO | WO-00/64474 A1 | 11/2000 |
| WO | WO-2011/049082 A1 | 4/2011 |

OTHER PUBLICATIONS

Nishimichi et al. Epitopes in α8 β1 and other RGD binding integrins delineate classes of integrin-blocking antibodies and major binding loops in α subunits. Sci Rep. Sep. 9, 2015;5:13756.*

Van Regenmortel MHV. Mapping Epitope Structure and Activity: From One-Dimensional Prediction to Four-Dimensional Description of Antigenic Specificity Methods. 9(3):465-72, 1996.*

Lerner, RA. Tapping the immunological repertoire to produce antibodies of predetermined specificity. Nature 1982; 299:592-596.*

Hung et al. Deletion of Integrin Alpha8 in PDGFRbeta+ Cells Attenuates Fibrosis in the Bleomycin Lung Injury Model B97. A Scar is Born: New Insights in Lung Fibrogenesis : pp. A3655-A3655, Abstracts.A3655, May 2014.*

Hartner et al. Deletion of the α8 Integrin Gene Does Not Protect Mice From Myocardial Fibrosis in DOCA Hypertension. Am J Hypertens (2009) 22 (1): 92-99.*

Hartner et al. Tubulointerstitial De Novo Expression of the a8 Integrin Chain in a Rodent Model of Renal Fibrosis—A Potential Target for Anti-Fibrotic Therapy?. PLOS ONE, 7(11):e48362, 2012.*

Benoit et al. Integrin α8β1 regulates adhesion, migration and proliferation of human intestinal crypt cells via a predominant hoA/ROCKdependent mechanism. Biol. Cell (2009) 101, 695-708.*

Lijnen, Paul J., Deletion of the α8 Integrin Gene Does Not Protect Mice From Myocardial Fibrosis in DOCA Hypertension. American Journal of Hypertension, 2009 | vol. 22 No. 1 | 8, p. 92. (Year: 2009).*

Horan et al. Partial Inhibition of Integrin avb6 Prevents Pulmonary Fibrosis without Exacerbating Inflammation. Am J Respir Crit Care Med vol. 177. pp. 56-65, 2008 (Year: 2008).*

Thibault et al. Upregulation of α8β1-integrin in cardiac fibroblast by angiotensin II and transforming growth factor-β1. Am J Physiol Cell Physiol. Nov. 2001;281(5):C1457-67. (Year: 2001).*

Denda et al. Identification of Osteopontin as a Novel Ligand for the Integrin α8β1 and Potential Roles for This Integrin—Ligand Interaction in Kidney Morphogenesis. Molecular Biology of the Cell. 9:1425-11435, 1998 (Year: 1998).*

Bouzeghranea et al., "Alpha8beta1 integrin is upregulated in myofibroblasts of fibrotic and scarring myocardium," J Mol Cell Cardiol. 36(3):343-53 (abstract only provided) (2004).

(Continued)

*Primary Examiner* — Maher M Haddad
(74) *Attorney, Agent, or Firm* — Clark & Elbing LLP; Susan M. Michaud

(57) ABSTRACT

Novel and effective anti-fibrosis agents are obtained. An anti-fibrosis agent containing an antagonist for integrin α8β1 is used. In addition, used is an antagonist containing an anti-integrin α8β1 antibody that specifically binds to at least one amino acid in a cap subdomain of an integrin α8 chain and a periphery thereof. Also, used is an anti-fibrosis agent containing an anti-integrin α8β1 antibody that specifically binds to R120 of an integrin α8 chain and a periphery thereof or S132 and a periphery thereof. Note that the above antagonists may each be an anti-integrin α8β1 antibody capable of binding to any of integrins α8β1 derived from a human, mouse, and rat.

16 Claims, 17 Drawing Sheets
Specification includes a Sequence Listing.

(56) References Cited

OTHER PUBLICATIONS

Levine et al., "Expression of the integrin alpha8beta1 during pulmonary and hepatic fibrosis," Am J Pathol. 156(6):1927-35 (2000).
Lu et al., "Integrin alpha8beta1 mediates adhesion to LAP-TGFbeta1," J Cell Sci. 115(Pt 23):4641-8 (2002).
Pardo et al., "Up-regulation and profibrotic role of osteopontin in human idiopathic pulmonary fibrosis," PLoS Med. 2(9):e251 (13 pages) (2005).
International Search Report for International Application No. PCT/JP2013/059368, dated Jul. 2, 2013 (3 pages).
International Preliminary Report of Patentability for PCT/JP2013/059368, dated Feb. 3, 2014 (14 pages).
Written Opinion and Reply for PCT/JP/059368, dated Jul. 2, 2013 (21 pages).
Extended European Search Report for European Application No. 13769951.8, dated Feb. 8, 2016 (14 pages).
Ginsberg et al., "Ligand binding to integrins: common and ligand specific recognition mechanisms," Cell Differ Dev. 32(3):203-13 (1990).
NCBI Blast NP_003629.2, retrieved on Jan. 18, 2016 (5 pages).
Sanchez-Cortes et al., "Using self-assembled monolayers to understand alpha8beta1-mediated cell adhesion to RGD and FEI motifs in nephronectin," ACS Chem Biol. 6(10):1078-86 (2011).
Sato et al., "Molecular basis of the recognition of nephronectin by integrin alpha8beta1," J Biol Chem. 284(21):14524-36 (2009).
Sato et al., "Supplemental data (Sato et al.)," J Biol Chem., May 22, 2009 (4 pages).
Schnapp et al., "Sequence and tissue distribution of the human integrin alpha 8 subunit: a beta 1-associated alpha subunit expressed in smooth muscle cells," J Cell Sci. 108(Pt 2):537-44 (1995).
Muller et al., "Integrin alpha8beta1 is critically important for epithelial-mesenchymal interactions during kidney morphogenesis," Cell. 88(5):603-13 (1997).

NCBI GEO DataSet Record GDS4389, Alcoholic hepatitis, <https://www.ncbi.nlm.nih.gov/sites/GDSbrowser>, series published Jun. 15, 2012, retrieved on Mar. 27, 2019 (1 page).
NCBI GEO DataSet Record GDS4389, Alcoholic hepatitis, sample subset and value distribution, available at <https://www.ncbi.nlm.nih.gov/geo/tools/profileGRAPH.cgi?ID-GDS4389:205032_at>, retrieved Mar. 27, 2019 (2 pages).
NCBI GEO DataSet Record GDS1492, Bleomycin effect on lungs: dose response and time course, sample subset and value distribution, available at <https://www.ncbi.nlm.nih.gov/geo/tools/profileGRAPH.cgi?ID-GDS1492:1423268_at>, retrieved Mar. 27, 2019 (2 pages).
NCBI GEO DataSet Record GDS1492, Bleomycin effect on lungs: dose response and time course, <https://www.ncbi.nlm.nih.gov/sites/GDSbrowser>, series published Dec. 29, 2005, retrieved on Mar. 27, 2019 (1 page).
NCBI GEO DataSet Record GDS1252, Idiopathic pulmonary fibrosis, sample subset and value distribution, available at <https://www.ncbi.nlm.nih.gov/geo/tools/profileGraph.cgi?ID-GDS1252:176%2C21>, retrieved Mar. 27, 2019 (2 pages).
NCBI GEO DataSet Record GDS1252, Idiopathic pulmonary fibrosis, <https://www.ncbi.nlm.nih.gov/sites/GDSbrowser>, series published Aug. 8, 2005, retrieved on Mar. 27, 2019 (1 page).
GEO Profiles, ITGA2—Alcoholic hepatitis, integrin subunit alpha 2 [*Homo sapiens*], ID: 85476870, available at<https://www.ncbi.nlm.gov/geoprofiles/85454780>, retrieved Mar. 27, 2019 (1 page).
GEO Profiles, ITGA5—Bleomycin effect on lungs: dose response and time course, integrin alpha 5 (fibronectin receptor alpha) [*Mus musculus*], ID: 14965362, <https://www.ncbi.nlm.nih.gov/geoprofiles/14965363>, retrieved Mar. 27, 2019 (1 page).
GEO Profiles, ITGA7—Idiopathic pulmonary fibrosis, integrin subunit alpha 7 [*Homo sapiens*], ID: 11089943, <https://www.ncbi.nlm.nih.gov/geoprofiles/11089943>, retrieved Mar. 27, 2019 (1 page).
Munger et al., "The integrin alpha v beta 6 binds and activates latent TGF beta 1: a mechanism for regulating pulmonary inflammation and fibrosis," Cell. 96(3):319-28 (1999).

* cited by examiner

FIG. 3
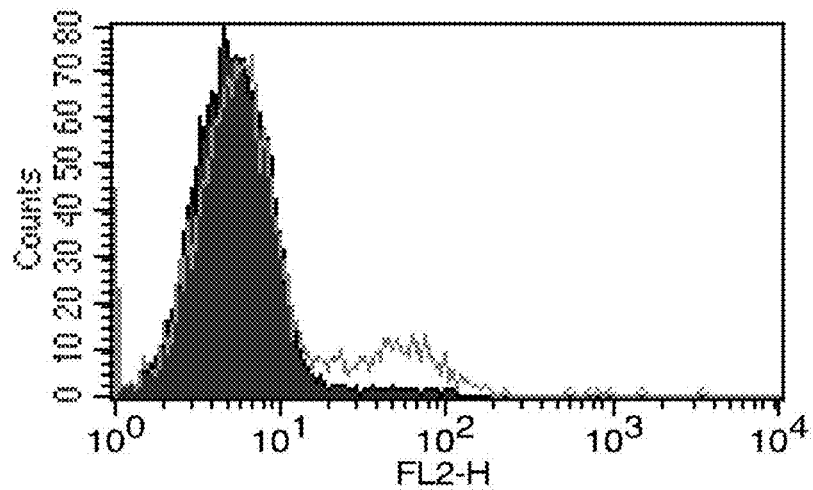
Wild Type
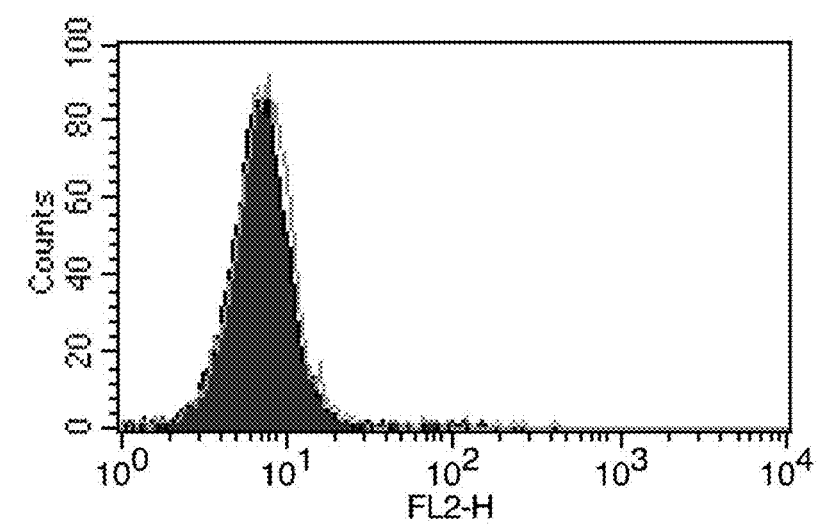
R120K
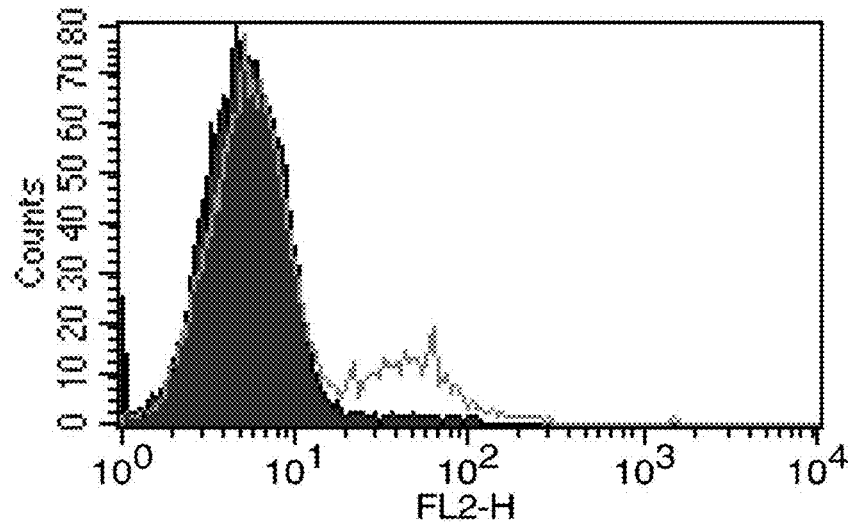
P161A

FIG. 4
R120K
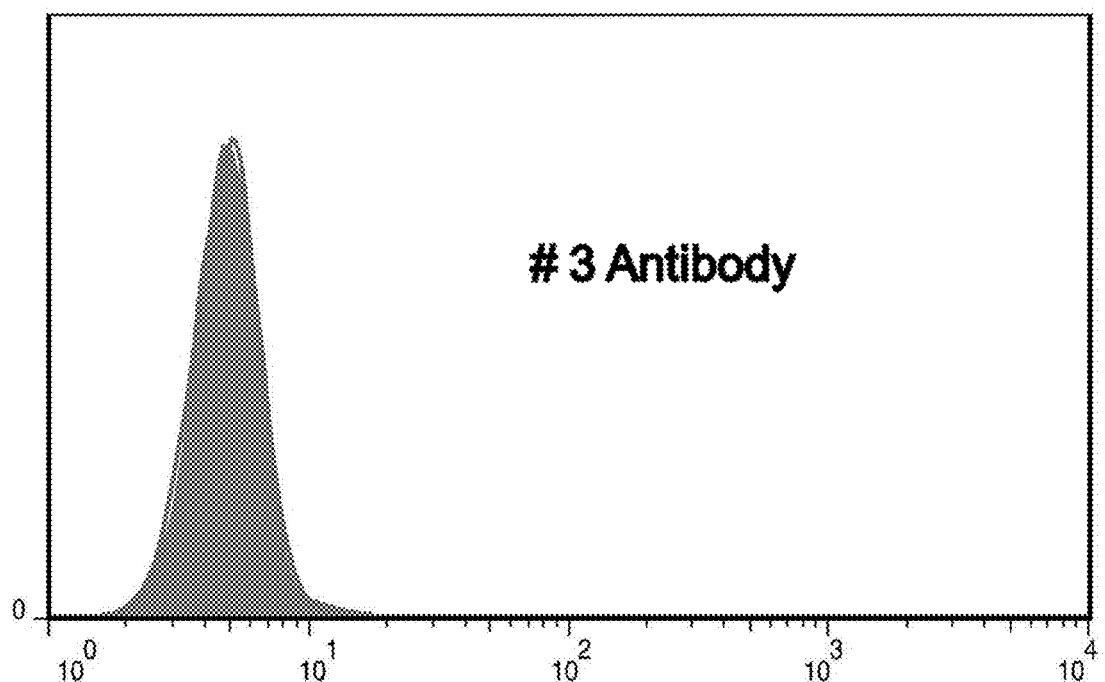
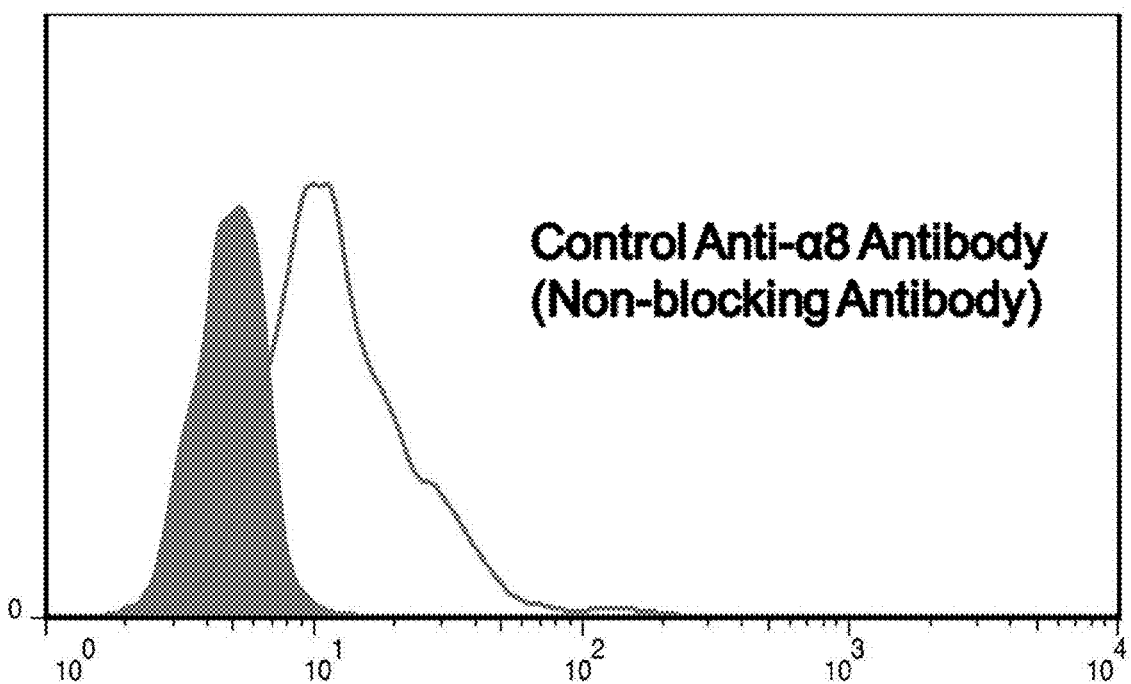

Blocking activity of the mAb against α8β1 function:

Cross reactivity between human and mouse α8β1:

FIG. 7

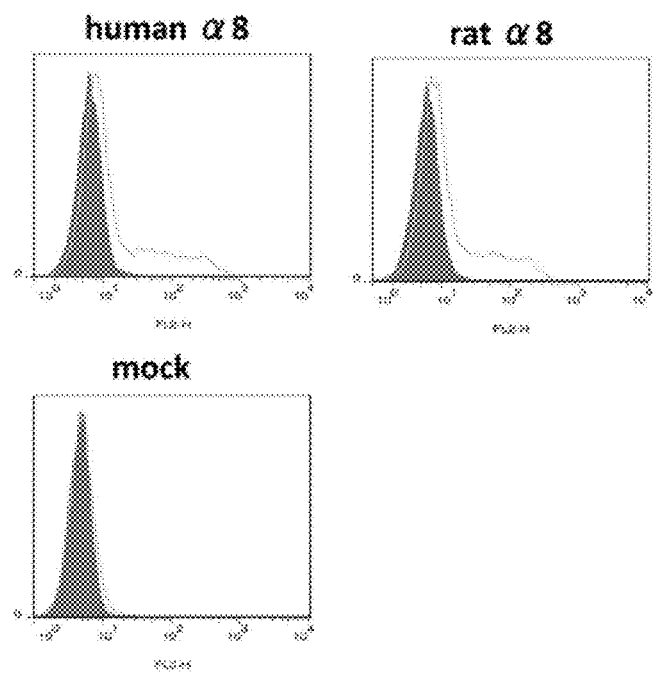

FIG. 8

| | | |
|---|---|---|
| cow | QIPFDNTNNRKIRVNGTKEPIEFKSNQWFGATV | (SEQ ID NO: 22) |
| pig | QIPFDNTNNRKIRVNGTKEPIEFKSNQWFGATV | (SEQ ID NO: 23) |
| dog | QIPFDNTNNRKIRVNGTKEPIEFKSNQWFGATV | (SEQ ID NO: 24) |
| mouse | QIPFDTTNNRKIRVNGTKEPIEFKSNQWFGATV | (SEQ ID NO: 25) |
| rat | QIPFDTTNNRKIRVNGTKEPIEFKSNQWFGATV | (SEQ ID NO: 26) |
| hamster | QIPFDTTNNRKIRVNGTKEPIEFKSNQWFGATV | (SEQ ID NO: 27) |
| chimpanzee | QIPFDTTNNRKIRVNGTKEPIEFKSNQWFGATV | (SEQ ID NO: 28) |
| gibbon | QIPFDTTNNRKIRVNGTKEPIEFKSNQWFGATV | (SEQ ID NO: 29) |
| monkey | QIPFDTTNNRKIRVNGTKEHIEFKSNQWFGATV | (SEQ ID NO: 30) |
| marmoset | QIPFDTTNNRKIRVNGTKEPIEFKSNQWFGATV | (SEQ ID NO: 31) |
| human | QIPFDTTNNRKIRVNGTKEPIEFKSNQWFGATV | (SEQ ID NO: 32) |

FIG. 10
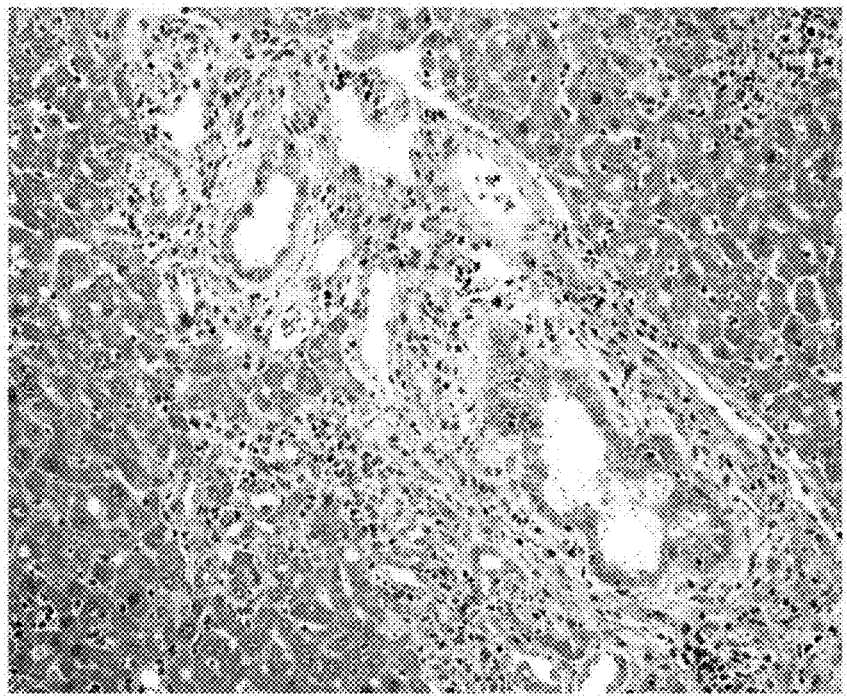
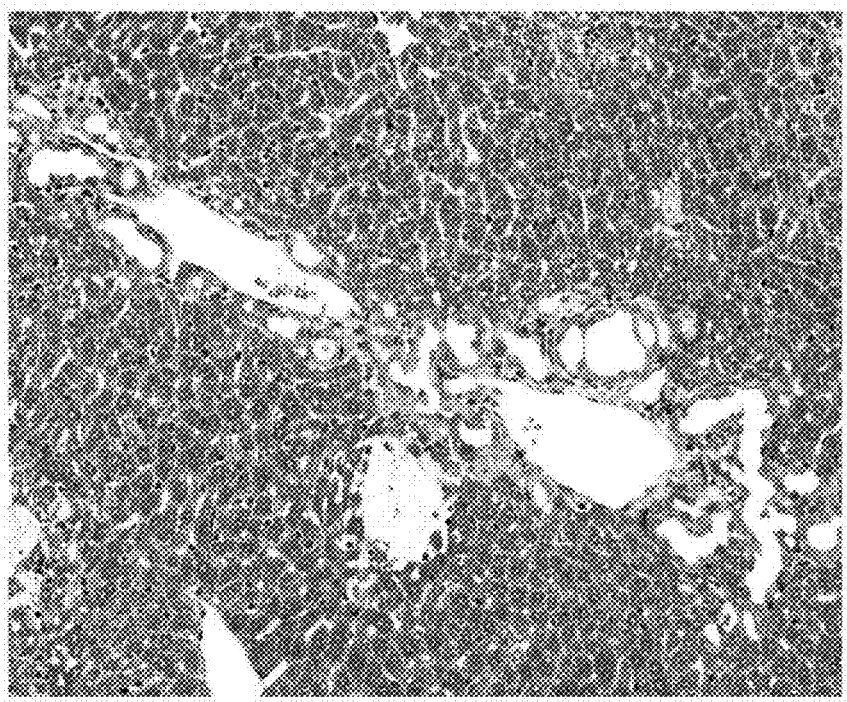

Without Antibody Administration    With Antibody Administration

FIG. 19
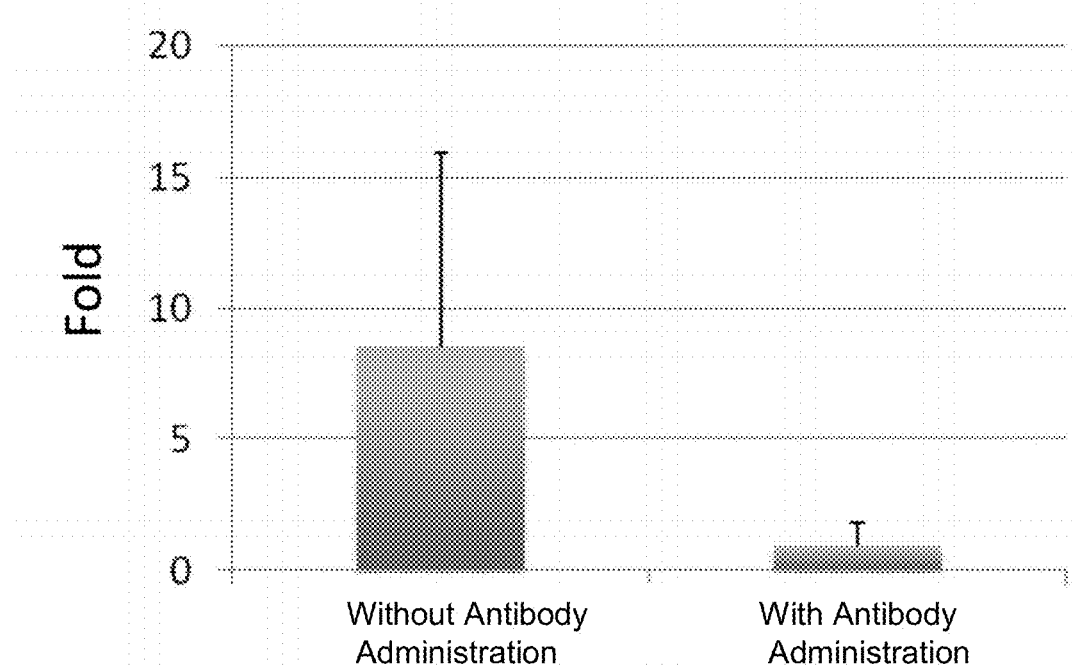
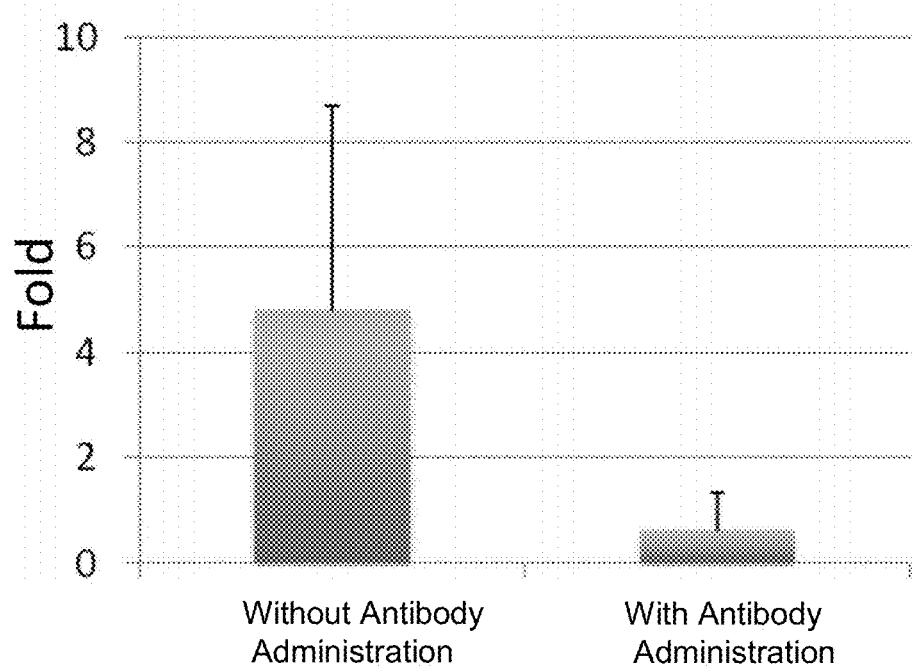

Blocking Effects of Antibodies on Adhesion between Nephronectin and α8β1-expressing K562 Cells

FIBROSIS SUPPRESSION BY INHIBITING INTEGRIN α-8 β-1 FUNCTION

TECHNICAL FIELD

The present invention relates to anti-fibrosis agents.

BACKGROUND ART

Fibrosis has been known as a disease caused by loss of normal function due to tissue sclerosis in which a mass of a connective tissue including tissue components such as collagen is increased and a normal tissue is replaced by the connective tissue. Fibrosis occurs in the liver, lung, kidney, heart, skin, etc. For example, occurrence of a large amount of fibrosis in a hepatic tissue results in hepatic cirrhosis.

Non Patent Literature 1 discloses a fibrosis study showing the results of investigating gene expression in pulmonary fibrosis. The results have demonstrated that levels of expression of 178 genes are up-regulated in the pulmonary fibrosis. If the significant difference (p<0.01 in TNoM and Student's t-test) is not considered, about 1000 genes have higher levels of expression. In addition, Non Patent Literature 2 discloses high levels of expression of integrin α8β1 during pulmonary fibrosis. Further, Patent Literature 1 discloses an antibody that inhibits binding of integrin α8β1 to its ligand.

CITATION LIST

Patent Literature

Patent Literature 1: WO2011/049082

Non Patent Literature

Non Patent Literature 1: "Up-regulation and profibrotic role of osteopontin in human idiopathic pulmonary fibrosis." Pardo et al., PLoS Med. 2005 September; 2(9): e251, Epub 2005 Sep. 6.

Non Patent Literature 2: "Expression of the integrin alpha8beta1 during pulmonary and hepatic fibrosis." Levine et al., Am J Pathol., 2000 June; 156(6): 1927-35.

SUMMARY OF INVENTION

Technical Problem

The above Non Patent Literatures 1 and 2 and Patent Literature 1, however, disclose nothing about the results of fibrosis treatment. Fibrosis is a particularly refractory disease among various diseases. To the present inventors' knowledge, only one drug is currently commercially available. The general name of the drug is Pirfenidone (Shionogi & Co., Ltd.). The only one drug, however, has been approved only in Japan and has a history that the U.S. FDA failed to approve the drug because its pharmacological effects were insufficient.

The present invention has been made in view of the above situations. It is an object of the present invention to provide a novel and effective anti-fibrosis agent.

Solution to Problem

As described in Examples below, the present inventors have successfully achieved the following in fibrosis model mice: 1) improvement in findings on fibrosis in a pathohistological image; 2) suppression of an increase in levels of expression of collagen α1 (I) and smooth muscle actin (α-SMA) genes and proteins; and 3) suppression of an increase in hydroxyproline content that reflects an amount of accumulation of collagen as a fibrosis index. Administration of a substance that inhibits integrin α8β1 functions is effective in these suppressions.

Note that as described above, Non Patent Literatures 1 and 2 disclose the results of investigating levels of expression of genes in tissue fibrosis and a pattern of their distribution. However, the levels and distribution of the genes may change because the genes share an expression regulation mechanism with other genes while their molecular functions are unnecessary. Because of this, generally speaking, a large number of genes have higher levels of expression during pathogenesis. Nobody has shown a piece of evidence that integrin α8β1 is functionally involved in fibrosis. Here, the present inventors are first to demonstrate the evidence in the below-described Examples. These Examples have clearly demonstrated, in animals, changes (improvements) in pathohistological findings and suppression of the above indexes. That is intriguing.

Specifically, an aspect of the present invention provides an anti-fibrosis agent containing an antagonist for integrin α8β1. Use of this anti-fibrosis agent can inhibit fibrosis.

In addition, another aspect of the present invention provides an anti-fibrosis agent containing an anti-integrin α8β1 antibody that specifically binds to at least one amino acid in a cap subdomain of an integrin α8 chain and a periphery thereof. Use of this anti-fibrosis agent can inhibit fibrosis.

In addition, another aspect of the present invention provides a drug for a disease accompanied by progression of fibrosis, comprising an antagonist for integrin α8β1. This drug may be used to treat a disease accompanied by progression of fibrosis.

Advantageous Effects of Invention

According to the present invention, a novel and effective anti-fibrosis agent can be used to inhibit fibrosis.

BRIEF DESCRIPTION OF DRAWINGS

FIG. 3 shows the results of FACS analysis when cells expressing the integrin α8β1 wild type, R120 mutant, or P161 mutant were reacted with an anti-integrin α8β1 antibody according to an Example.

FIG. 4 shows the results of FACS analysis when cells expressing the integrin α8β1 R120 mutant were reacted with an anti-integrin α8β1 antibody according to an Example or with a control anti-α8 antibody.

FIG. 7 shows the results of FACS analysis of an anti-integrin α8β1 antibody according to an Example regarding cross-reactivity to integrins α8β1 derived from a human and a rat.

FIG. 8 shows the results of alignment of amino acid sequences at R120 and its periphery of integrins α8 derived from various species.

FIG. 10 is photographs of Masson's trichrome staining of liver sections of BDL mice when an anti-integrin α8β1 antibody according to an Example was or was not administered.

FIG. 19 is graphs illustrating the results of measuring levels of expression of Col α1(I) and α-SMA genes in the lungs of pulmonary fibrosis model mice when an anti-integrin α8β1 antibody according to an Example was or was not administered.

DESCRIPTION OF EMBODIMENTS

Figure 1:
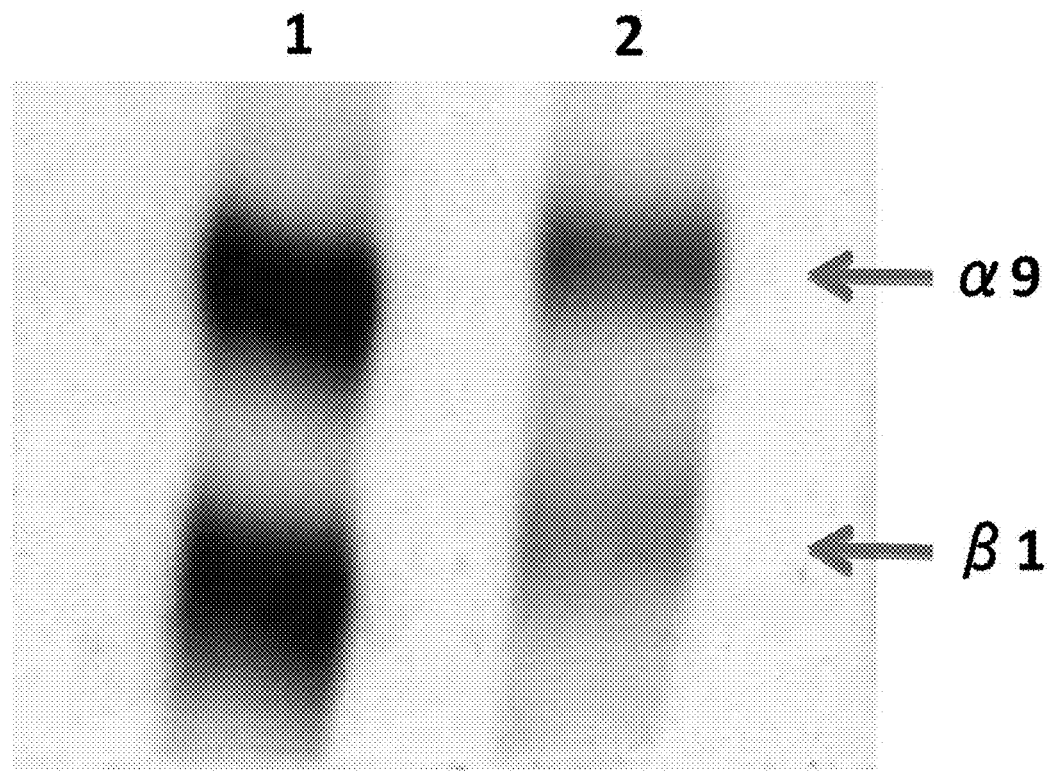
FIG. 1 shows the results of coimmunoprecipitation using an anti-human integrin α9 antibody Y9A2 and detergent lysates of a human integrin α9-introduced chicken cell line.

Hereinafter, embodiments of the present invention will be described in detail. Note that descriptions are not repeated so as to avoid redundancy.

An embodiment of the present invention provides a novel anti-fibrosis agent. This anti-fibrosis agent contains, for example, an antagonist for integrin α8β1. The integrin α8β1 antagonist can suppress fibrosis as demonstrated in the following Examples. Use of this anti-fibrosis agent containing the above component can thus inhibit fibrosis.

Note that the "fibrosis" has been widely known as a disease caused by loss of normal function due to tissue sclerosis in which a mass of a connective tissue including tissue components such as collagen is increased and a normal tissue is replaced by the connective tissue. Fibrosis occurs in, for example, the liver, lung, kidney, heart, and skin. Also, occurrence of a large amount of fibrosis in a hepatic tissue, for example, results in hepatic cirrhosis. In addition to hepatic cirrhosis, each tissue may have a malignant tumor while fibrosis progresses.

The "integrin α8β1", in general, is a heterodimer consisting of α and β chains and is a receptor protein present on the cell surface. Its DNA and amino acid sequences have been deposited in, for example, GenBank, a database of the National Center for Biotechnology Information (NCBI) and can be referred to. For example, the amino acid sequence of α chain may be an amino acid sequence set forth in SEQ ID NO: 7. For example, the amino acid sequence of β chain may be an amino acid sequence set forth in SEQ ID NO: 8. The α and β chains may or may not contain a signal peptide. Examples of a ligand can include osteopontin, fibronectin, vitronectin, and tenascin.

As used herein, an antagonist according to an embodiment is not particularly limited, but may preferably be an anti-integrin α8β1 antibody that inhibits binding of integrin α8β1 to its ligand. In addition, the antagonist may preferably be an anti-integrin α8β1 antibody that specifically binds to at least one amino acid in a cap subdomain of the integrin α8 chain and a periphery thereof. In addition, the antagonist may preferably be an anti-integrin α8β1 antibody that specifically binds to R120 of the integrin α8 chain and a periphery thereof or S132 and a periphery thereof. In addition, the antagonist may preferably be an anti-integrin α8β1 antibody capable of binding to any of integrins α8β1 derived from a human, mouse, and rat. In addition, the antagonist may preferably be an anti-integrin α8β1 antibody that inhibits a function of integrin α8β1. In addition, the antagonist may preferably be an anti-integrin α8β1 antibody that does not bind to R120K mutant or S132A mutant of the integrin α8 chain while binding to a wild type of the integrin α8 chain. In addition, the antagonist may preferably be an anti-integrin α8β1 antibody comprising amino acid sequences of heavy chain CDRs 1, 2, and 3 set forth in SEQ ID NOs: 1, 2, and 3 and amino acid sequences of light chain CDRs 1, 2, and 3 set forth in SEQ ID NOs: 4, 5, and 6, respectively. In addition, the antagonist may be, but is not limited to, an antibody, protein, low-molecular-weight compound, polymer compound, or nucleic acid as long as the antagonist can inhibit binding of integrin α8β1 to its ligand.

In addition, an embodiment of the present invention provides an anti-fibrosis agent containing an anti-integrin α8β1 antibody that specifically binds to R120 of the integrin α8 chain and a periphery thereof or S132 and a periphery thereof. As demonstrated in the below-described Examples, the anti-integrin α8β1 antibody that specifically binds to R120 of the integrin α8 chain and a periphery thereof or S132 and a periphery thereof can suppress fibrosis. Use of this anti-fibrosis agent containing the above component can thus inhibit fibrosis.

In addition, an embodiment of the present invention provides an anti-fibrosis agent containing an anti-integrin α8β1 antibody that specifically binds to at least one amino acid in a cap subdomain of the integrin α8 chain or the amino acid and a periphery thereof. Use of this anti-fibrosis agent can inhibit fibrosis.

In addition, an embodiment of the present invention provides an anti-fibrosis agent containing an anti-integrin α8β1 antibody that does not bind to R120K mutant or S132A mutant of the integrin α8 chain while binding to a wild type of the integrin α8 chain. As demonstrated in the below-described Examples, the anti-integrin α8β1 antibody that does not bind to R120K mutant or S132A mutant of the integrin α8 chain while binding to a wild type of the integrin α8 chain can suppress fibrosis. Use of this anti-fibrosis agent containing the above component can thus inhibit fibrosis.

In addition, an embodiment of the present invention provides an anti-fibrosis agent containing an anti-integrin α8β1 antibody that does not bind to at least one cap subdomain mutant of the integrin α8 chain while binding to a wild type of the integrin α8 chain. Use of this anti-fibrosis agent can inhibit fibrosis. Note that the cap subdomain mutant of the integrin α8 chain refers to an integrin α8 chain mutant in which at least one amino acid in a cap subdomain is mutated. Here, the antibody that does not bind to the cap subdomain mutant may not bind to the at least one mutant. The foregoing antibody may bind to another mutant in which another amino acid in the cap subdomain is mutated.

In addition, an embodiment of the present invention provides an anti-fibrosis agent containing a polynucleotide encoding an anti-integrin α8β1 antibody that inhibits a function of integrin α8β1. As demonstrated in the below-described Examples, the anti-integrin α8β1 antibody that inhibits a function of integrin α8β1 can suppress fibrosis. Use of the anti-fibrosis agent containing the above component results in expression of the above anti-integrin α8β1 antibody encoded by the above polynucleotide. Accordingly, fibrosis can be suppressed.

In addition, an embodiment of the present invention provides an anti-fibrosis agent containing a precursor of an integrin α8β1 antagonist. The integrin α8β1 antagonist can suppress fibrosis as demonstrated in the following Examples. When the anti-fibrosis agent containing the above component is used, the above antagonist is produced from the above precursor. As a result, fibrosis can be suppressed.

In addition, an embodiment of the present invention provides an anti-fibrosis agent containing a functional inhibitor for integrin α8β1. Inhibiting a function of integrin α8β1 can suppress fibrosis as demonstrated in the following Examples. Use of this anti-fibrosis agent containing the above component can thus inhibit fibrosis.

In addition, an embodiment of the present invention provides a method for suppressing or treating fibrosis, the method including using an antagonist or anti-fibrosis agent according to the above embodiment. This method can suppress fibrosis, thereby capable of treating a disease accompanied by fibrosis or progression of fibrosis.

In addition, an embodiment of the present invention provides a collagen accumulation inhibitor containing an integrin α8β1 antagonist. Also, an embodiment of the present invention provides a method for inhibiting accumulation of collagen. The integrin α8β1 antagonist can suppress accumulation of collagen as demonstrated in the following Examples. Use of this collagen accumulation inhibitor containing the above component can thus inhibit accumulation of collagen.

In addition, an embodiment of the present invention provides an inhibitor for expression of collagen α1(I) or α-SMA, the inhibitor containing an integrin α8β1 antagonist. Also, an embodiment of the present invention provides a method for down-regulating expression of collagen α1(I) or α-SMA. The integrin α8β1 antagonist can down-regulate expression of collagen α1(I) or α-SMA as demonstrated in the following Examples. Use of this collagen α1(I)- or α-SMA-expression inhibitor containing the above component can thus down-regulate expression of collagen α1(I) or α-SMA. Note that the amino acid and DNA sequences of collagen α1(I) and α-SMA can be obtained from GenBank, etc.

In addition, an embodiment of the present invention provides a hydroxyproline production inhibitor containing an integrin α8β1 antagonist. Also, an embodiment of the present invention provides a method for suppressing production of hydroxyproline. The integrin α8β1 antagonist can suppress production of hydroxyproline as demonstrated in the following Examples. Use of this hydroxyproline production inhibitor containing the above component can thus inhibit production of hydroxyproline. Note that hydroxyproline may be quantified according to, for example, a procedure described in the following Examples or a protocol disclosed in "Inayama et al., Keio J Med., Vol. 27, No. 1, 43-46 (1978)".

In addition, an embodiment of the present invention provides a method including causing an integrin α8β1 antagonist to contact abnormal cells, wherein the abnormal cells express integrin α8β1 and have higher levels of expression of collagen α1(I) or α-SMA than normal cells; and the expression of collagen α1(I) or α-SMA is inhibited. This method can inhibit expression of collagen α1(I) or α-SMA, thereby ameliorating a disease.

In addition, an embodiment of the present invention provides a method including causing an integrin α8β1 antagonist to contact abnormal cells, wherein the abnormal cells express integrin α8β1 and have higher levels of production of hydroxyproline than normal cells; and the production of hydroxyproline is inhibited. This method can inhibit production of hydroxyproline, thereby ameliorating a disease.

As used herein, the term "R120 of the integrin α8 chain and a periphery thereof" preferably refers to a region encompassing an amino acid sequence of position 114, 115, 116, 117, 118, 119, 120, 121, 122, 123, 124, 125, or 126 of the integrin α8 chain. In addition, the term may refer to a region containing an amino acid sequence set forth in SEQ ID NO: 9 of the integrin α8 chain. This periphery is not particularly limited as long as the periphery contains a region that is an epitope for the above anti-integrin α8β1 antibody. Note that the above positions 114 to 126 are the position numbers that are counted using the signal peptide-containing integrin α8 chain as a reference. Accordingly, when the integrin α8 chain includes no signal peptide, the above positions 114 to 126 mean amino acids at respective positions 76, 77, 78, 79, 80, 81, 82, 83, 84, 85, 86, 87, and 88. Note that the phrase "an antibody that specifically binds to a specific region" includes that an antibody recognizes a specific region as an epitope. The phrase "recognize an epitope" includes that part of an epitope is recognized. The phrase "an antibody that specifically binds to a specific amino acid and a periphery thereof" includes that an antibody specifically recognizes and binds to the structure of a specific amino acid and a periphery thereof.

As used herein, the term "S132 of the integrin α8 chain and a periphery thereof" may refer to a region encompassing an amino acid sequence of position 126, 127, 128, 129, 130, 131, 132, 133, 134, 135, 136, 137, or 138 of the integrin α8 chain. Note that the above positions 126 to 138 are the position numbers that are counted using the signal peptide-containing integrin α8 chain as a reference. Accordingly, when the integrin α8 chain includes no signal peptide, the above positions 126 to 138 mean amino acids at respective positions 88, 89, 90, 91, 92, 93, 94, 95, 96, 97, 98, 99, and 100. A periphery of the above amino acid is, for example, a region that can be recognized as an epitope by an antibody according to an embodiment of the present invention. The periphery of the above amino acid may include a specific amino acid and 1, 2, 3, 4, 5, or 6 amino acids before and after the specific amino acid.

As used herein, the cap subdomain of the integrin α chain may contain cap subdomain inserts 1 to 4. An antibody-binding site of the α chain according to an embodiment of the present invention is preferably within the insert 1 in view of stably suppressing fibrosis. As used herein, the insert 1 may be, for example, a peptide fragment containing position 113, 114, 115, 116, 117, 118, 119, 120, 121, 122, 123, 124, 125, 126, 127, 128, 129, 130, 131, or 132 of the integrin α chain. When the integrin α8 chain includes no signal peptide, the above positions 113 to 132 may mean amino acids at positions 75 to 94, respectively. As used herein, the insert 2 may be, for example, a peptide fragment containing position 154, 155, 156, 157, 158, 159, 160, 161, 162, 163, 164, 165, 166, 167, 168, 169, 170, or 171 of the integrin α chain. When the integrin α8 chain includes no signal peptide, the above positions 154 to 171 may mean amino acids at positions 116 to 133, respectively. As used herein, the insert 3 may be, for example, a peptide fragment containing position 187, 188, 189, 190, 191, 192, 193, 194, 195, 196, 197, 198, or 199 of the integrin α chain. When the integrin α8 chain includes no signal peptide, the above positions 187 to 199 may mean amino acids at positions 149 to 161, respectively. As used herein, the insert 4 may be, for example, a peptide fragment containing position 233, 234, 235, 236, 237, 238, 239, 240, 241, 242, 243, 244, 245, 246, 247, 248, 249, or 250 of the integrin α chain. When the integrin α8 chain includes no signal peptide, the above positions 233 to 250 may mean amino acids at positions 195 to 212, respectively. Xiao et al. (Nature, 2004, Nov. 4; 432 (7013): 59-67) has reported an example of the positions of the cap subdomain of the integrin family.

In the text of the specification of the present application, the state in which a function of integrin α8β1 is inhibited by an anti-integrin α8β1 antibody includes a state in which when integrin α8β1 is reacted with its ligand, an amount of their binding is significantly lower than that at normal conditions. The term "significantly lower" may refer to a state in which the above amount of binding is decreased to 0.7, 0.6, 0.5, 0.4, 0.3, 0.2, 0.1, 0.01, or 0 fold. This rate may be any one of the above values or lower, or may be between any two of the above values. In view of particularly clearly inhibiting the function of integrin α8β1, the amount of binding is decreased preferably to 0.5 fold or lower and more preferably to 0.1 fold or lower. Note that as described in a method of the following Examples, the above amount of binding, for example, may be determined by measuring absorbance after staining. The absorbance represents the number of integrin α8β1-expressing cells that attach to a ligand-immobilized plate after the cells are made to contact the plate. In addition, as used herein, the term "significantly" may include a case of $p<0.05$ when Student's t test (one-sided or two-sided) is used to evaluate a statistically significant difference. Also, the term may include a state in which there is a substantial difference.

As used herein, the "state in which an antibody does not bind to an antigen" may include a state in which an antibody does not completely bind to an antigen or an amount of binding of the antibody to an antigen is markedly low. The binding of an antibody to an antigen may be measured by flow cytometry (FACS) analysis after the antibody is reacted with, for example, antigen-expressing cells. Here, the FACS analysis typically includes the steps of: irradiating a cell flowing inside a flow cell with a laser beam; measuring parameters as obtained from forward-scattered light and side-scattered light; and determining cellular properties. In one hand, a user may determine a state in which an antibody does not bind to an antigen when a peak as obtained by reacting the antibody with antigen-expressing cells is neither substantially nor significantly shifted from a peak as obtained by reacting the antibody with antigen-free cells. On the other hand, a user may determine a state in which an antibody does bind to an antigen when a peak as obtained by reacting the antibody with antigen-expressing cells is substantially or significantly shifted from a peak as obtained by reacting the antibody with antigen-free cells. Alternatively, a surface plasmon resonance-measuring device is used to determine a state in which an antibody does not bind to an antigen. Then, the state may include a state in which an association rate constant (Ka) is 0.2, 0.1, 0.05, or 0.01 time the association rate constant when the binding occurs. This rate may be any one of the above values or lower, or may be between any two of the above values.

As used herein, the state in which levels of expression of a gene are inhibited may include a state in which levels of expression of a gene are significantly inhibited. Also, the level may be decreased by 40, 50, 60, 70, 80, 90, or 100%. This rate may be any one of the above values or higher, or may be between any two of the above values. In view of suppressing fibrosis, the rate is preferably 50% or higher and more preferably 70% or higher. In addition, compared with levels of expression of a gene in a tissue with fibrosis, the levels of expression may be decreased to 0.7, 0.6, 0.5, 0.4, 0.3, 0.2, 0.1, 0.01, or 0 fold. This rate may be any one of the above values or lower, or may be between any two of the above values. In view of suppressing fibrosis, the level is decreased preferably to 0.5 fold or lower and more preferably to 0.1 fold or lower. Note that as used herein, the state in which levels of expression of a gene is inhibited is substantially the same state in which levels of expression of the above gene is decreased.

As used herein, the state in which production of hydroxyproline is inhibited may include a state in which production of hydroxyproline is significantly inhibited. Also, the level may be decreased by 40, 50, 60, 70, 80, 90, or 100%. This rate may be any one of the above values or higher, or may be between any two of the above values. In addition, compared with levels of production of hydroxyproline in a tissue with fibrosis, the levels of production may be decreased to 0.9, 0.8, 0.7, 0.6, 0.5, 0.2, 0.1, or 0 fold. This rate may be any one of the above values or lower, or may be between any two of the above values. In view of suppressing fibrosis, the levels are preferably decreased to 0.9 fold or lower. Note that as used herein, the state in which levels of production of hydroxyproline are inhibited is substantially the same state in which the above production of hydroxyproline is inhibited.

As used herein, the term "increase" may include a state in which a level is increased to, for example, 1.2, 1.3, 1.4, 1.5, 2, 2.5, 3, 5, 10, or 40 folds. This rate may be any one of the above values or higher, or may be between any two of the above values.

As used herein, the term "precursor of a ligand" may include a substance that can have the same structure as of the above ligand after a structural change is caused by reacting the precursor with any substance in vivo or in vitro.

As used herein, the term "amino acid" means the general term for an organic compound having an amino group and a carboxyl group. When an anti-integrin α8β1 antibody according to an embodiment of the present invention contains a "specific amino acid sequence", any of amino acids in the amino acid sequence may be chemically modified. Even in such a case, an anti-integrin α8β1 antibody according to an embodiment of the present invention can be said to contain the above "specific amino acid sequence". Generally speaking, known examples of an in vivo amino acid chemical modification of a protein include: N-terminal modifications (e.g., acetylation, myristoylation); C-terminal modifications (e.g., amidation, glycosylphosphatidylinositol addition); and side chain modifications (e.g., phosphorylation, glycosylation).

As used herein, the term "polynucleotide" may include a nucleotide(s) or a base(s) or those having a plurality of their equivalents. Examples of the nucleotide and base include a DNA base and an RNA base. Examples of the above equivalents include a nucleotide analog or a DNA or RNA base with a chemical modification such as methylation. Examples of the nucleotide analog include a synthetic nucleotide. The term "nucleotide sequence" refers to a sequence of nucleotides constituting a polynucleotide or a sequence of their equivalents. In the description of a nucleotide sequence, the term "A, T, G, and C" includes adenine or an equivalent thereof, thymine or an equivalent thereof, guanine or an equivalent thereof, and cytosine or an equivalent thereof, respectively. In addition, T and U (uracil) are switchable depending on their usage. Note that a polynucleotide can be synthesized using a DNA/RNA synthesizer. In addition, the polynucleotide can be purchased from a service company (e.g., Invitrogen, Inc.) where DNA or RNA polynucleotides can be synthesized. Further, the polynucleotide may refer to a vector or a plasmid.

Examples of the above vector that can be used include: *E. coli*-derived plasmids (e.g., pET-Blue); *Bacillus subtilis*-derived plasmids (e.g., pUB 110); yeast-derived plasmids (e.g., pSH19); expression plasmids for animal cells (e.g., pA1-11); bacteriophages such as λ phage; and virus-derived vectors. These vectors each contain, for example, a promoter, a replication origin, and/or an antibiotic resistance gene, which are essential components for protein expression. The above vector may be an expression vector.

Cells can be transformed with a vector or polynucleotide encoding an anti-integrin α8β1 antibody according to an embodiment of the present invention. These transformants can be used to prepare an anti-integrin α8β1 antibody according to an embodiment of the present invention by using a known method in the art. The transformants may be cells derived from a human or another mammal (e.g., a rat, mouse, guinea pig, rabbit, cow, monkey, etc.). Examples of the mammalian cells include Chinese hamster ovary (CHO) cells and monkey cells (e.g., COS-7 cells). Also, the transformants may be *Escherichia coli* cells, yeast, etc.

Introduction of the above polynucleotide or vector into cells and production of an antibody can be performed in accordance with a known method in the art. Examples of a method for introducing a polynucleotide or a vector into a cell include a calcium phosphate method, lipofection, electroporation, an adenovirus-mediated method, a retrovirus-mediated method, microinjection, and the like ("Genetic Engineering Handbook", 4th Edition, YODOSHA CO., LTD. (2003): 152-179). Methods (described in, for example, "Protein Experiment Handbook", YODOSHA CO., LTD., (2003), 128-142) can be used as a process for producing an antibody by using cells.

Examples of a method for purifying an antibody include: ammonium sulfate precipitation; ethanol precipitation; Protein A, Protein G, or gel filtration chromatography; anion or cation-exchange chromatography; phosphocellulose chromatography; hydrophobic interaction chromatography; affinity chromatography; hydroxyapatite chromatography; lectin chromatography; and the like ("Protein Experiment Handbook", YODOSHA CO., LTD., 2003, 27-52).

As used herein, the term "binding" means a link between substances. The link may be either a covalent bond or a non-covalent bond, and examples of the link include an ionic bond, a hydrogen bond, a hydrophobic interaction, and a hydrophilic interaction. As used herein, the term "recognize" in an antigen-antibody reaction may be used as a regular meaning in the field of antibody engineering and may mean, for example, specific binding.

As used herein, the term "at least one" may refer to 1, 2, 3, 4, 5, 6, 7, 8, 9, 10, or 20. The term may mean any of the above values or higher, or may be within any two of the above values.

Integrin α8β1 bound to an anti-integrin α8β1 antibody according to an embodiment of the present invention may be derived from, but is not limited to, at least one of a human, mouse, guinea pig, hamster, rat, rodent, rabbit, pig, sheep, cow, horse, cat, dog, marmoset, monkey, and chimpanzee. Among them, a human is preferable in view of using an anti-integrin α8β1 antibody as a drug. In addition, a mouse and a rat are preferable from a viewpoint that the mouse and the rat are particularly suitable as a model animal that can be used in a non-clinical study.

According to an embodiment of the present invention, an anti-integrin α8β1 antibody may be a monoclonal antibody. The monoclonal antibody can act on integrin α8β1 more efficiently than a polyclonal antibody.

An anti-integrin α8β1 antibody according to an embodiment of the present invention may be an antibody fragment with antigen-binding activity (hereinafter, sometimes referred to as an "antigen-binding fragment"). In this case, there are effects that increase stability or antibody production efficiency.

An anti-integrin α8β1 antibody according to an embodiment of the present invention may bind to a wild type or mutant of integrin α8β1. The term "mutant" includes being responsible for a DNA sequence variation among individuals. In this regard, however, it is preferable that the antibody does not bind to R120 K mutant or S132A mutant of the integrin α8 chain. Homology between an amino acid sequence of a wild type or mutant of the α chain and an amino acid sequence set forth in SEQ ID NO: 7 is preferably 80% or higher, more preferably 90% or higher, and still more preferably 95% or higher. Homology between an amino acid sequence of a wild type or mutant of the 13 chain and an amino acid sequence set forth in SEQ ID NO: 8 is preferably 80% or higher, more preferably 90% or higher, and still more preferably 95% or higher.

The class of an anti-integrin α8β1 antibody according to an embodiment of the present invention is not particularly limited. Examples of the class may include IgM, IgD, IgG, IgA, and IgE.

In addition, according to an embodiment of the present invention, an anti-fibrosis agent contains an anti-integrin α8β1 antibody including: heavy chain CDRs 1, 2, and 3 set forth in SEQ ID NOs: 1, 2, and 3, respectively; and light chain CDRs 1, 2, and 3 set forth in SEQ ID NOs: 4, 5, and 6, respectively. As demonstrated in the below-described Examples, the anti-integrin α8β1 antibody containing these specific amino acid sequences can suppress fibrosis. Use of this anti-fibrosis agent containing the above component can thus inhibit fibrosis.

In addition, according to an embodiment of the present invention, an anti-fibrosis agent contains an anti-integrin α8β1 antibody including: heavy chain CDRs 1, 2, and 3 set forth in SEQ ID NOs: 10, 11, and 12, respectively; and light chain CDRs 1, 2, and 3 set forth in SEQ ID NOs: 13, 14, and 15, respectively. Use of this anti-fibrosis agent can inhibit fibrosis. In addition, according to an embodiment of the present invention, an anti-fibrosis agent contains an anti-integrin α8β1 antibody including: heavy chain CDRs 1, 2, and 3 set forth in SEQ ID NOs: 16, 17, and 18, respectively; and light chain CDRs 1, 2, and 3 set forth in SEQ ID NOs: 19, 20, and 21, respectively. Use of this anti-fibrosis agent can inhibit fibrosis.

Note that it has been generally known that even if the amino acid sequence of an antibody has some deletions, substitutions, insertions and/or additions, functions of the antibody remain in a certain degree. Because of this, the above anti-integrin α8β1 antibody having the specific amino acid sequences may have, for example, some deletions, substitutions, and/or additions. For example, the antibody having such deletions, substitutions, and/or additions can be produced using site-specific mutagenesis, random mutagenesis, or biopanning using an antibody phage library. In the site-specific mutagenesis, a KOD-Plus-Mutagenesis kit (TOYOBO CO., LTD.), for example, can be used. In order to select an antibody having substantially the same activity as the wild type from mutant antibodies having deletions, substitutions, and/or additions, various kinds of characterization can be carried out using FACS analysis, ELISA, etc.

In addition, as long as the above anti-integrin α8β1 antibody has a function of inhibiting binding of integrin α8β1 to its agonist, the antibody may contain an amino acid sequence having one or more amino acid deletions, substitutions, insertions, or additions, compared with the wild type. Also, as long as the antibody has a function of inhibiting binding of integrin α8β1 to its agonist, the amino acid sequence of the antibody of interest may exhibit 90% or higher identity with the amino acid sequence of the wild type. Further, as long as the antibody has a function of inhibiting binding of integrin α8β1 to its agonist, the antibody may have an amino acid sequence encoded by a nucleotide sequence of nucleic acid hybridized under stringent conditions with nucleic acid containing a nucleotide sequence complementary to a nucleotide sequence encoding the amino acid sequence of the wild type.

Furthermore, as long as the above anti-integrin α8β1 antibody has a function of inhibiting binding of integrin α8β1 to its agonist, the amino acid sequence set forth in the above SEQ ID NO: 1, 5, 10, 14, 16, or 20 may have one or two amino acid deletions, substitutions, insertions, or additions. Moreover, as long as the above anti-integrin α8β1 antibody has a function of inhibiting binding of integrin α8β1 to its agonist, the amino acid sequence set forth in the above SEQ ID NO: 2, 3, 4, 6, 11, 12, 13, 15, 17, 18, 19, or 21 may have one or two or three amino acid deletions, substitutions, insertions, or additions.

If the above anti-integrin α8β1 antibody has one or more amino acid deletions, substitutions, insertions, or additions, the "number of the amino acid modifications" may be 15, 10, 8, 6, 4, or 2. The number is any of the above values or less. A smaller number is preferable. This is because the less the "number of the amino acid modifications", the more similar characteristics the antibody of interest has, compared to those of the original anti-integrin α8β1 antibody. Note that it has been generally known that a polypeptide having its amino acid sequence modified by one or more amino acid residue deletions, additions, insertions, or substitutions with other amino acids can maintain its biological activity (Mark et al., Proc Natl Acad Sci USA., 1984, September, 81(18), 5662-5666; Zoller et al., Nucleic Acids Res., 1982, Oct. 25, 10(20), 6487-6500; and Wang et al., Science, 1984, Jun. 29, 224(4656), 1431-1433).

When one or more amino acids of the above anti-integrin α8β1 antibodies are substituted by other amino acids, the amino acids are preferably substituted by other amino acids that are conserved in their side chain characteristics. Examples of the characteristics of the amino acid side chain can include hydrophobic amino acids (e.g., A, I, L, M, F, P, W, Y, V), hydrophilic amino acids (e.g., R, D, N, C, E, Q, G, H, K, S, T), amino acids having an aliphatic side chain (e.g., G, A, V, L, I, P), amino acids having a hydroxy-containing side chain (e.g., S, T, Y), amino acids having a sulfur-containing side chain (e.g., C, M), amino acids having a carboxylic-acid-containing or amide-containing side chain (e.g., D, N, E, Q), amino acids having a base-containing side chain (e.g., R, K, H), and amino acids having an aromatic side chain (e.g., H, F, Y, W)(the respective letters between parentheses denote one-letter abbreviations of amino acids). A substitution of an amino acid by an amino acid within each group is generally referred to as a "conservative substitution".

With regard to the above anti-integrin α8β1 antibodies, the term "90% or higher" used to describe identity of an amino acid sequence may refer to, for example, 90, 95, 98, 99, or 100%. In addition, the term may indicate any of the above values or higher or a value between any two of the above values. A larger number is preferable. This is because the higher a value represented by the "90% or higher" becomes, the more similar characteristics the antibody of interest has, compared to those of the original anti-integrin α8β1 antibody.

As used herein, the term "identity" may refer to a ratio of the number of identical amino acids between two or among a plurality of amino acid sequences to the total number of amino acids as calculated by using a method known in the art. Before the calculation of the ratio, amino acid sequences selected from the group of amino acid sequences compared are aligned. If the ratio of the identical amino acids needs optimization, gaps are inserted in some portions of the amino acid sequence. An alignment method, a ratio calculation method, a comparison method, and a related computer program have been conventionally well-known in the art (e.g., BLAST, GENETYX). As used herein, unless otherwise indicated, the term "identity" can be represented by a value determined by BLAST of the NCBI (http://www.ncbi.nlm.nih gov/). Blastp can be used in default setting as an algorithm when BLAST is used for amino acid sequence comparison. The numerical values of the measured results are designated under "Positives" or "Identities".

As used herein, the following conditions, for example, can be used as a stringent condition. (1) For washing, a low ionic strength solution and a high temperature are used (e.g., a 0.015 M sodium chloride/0.0015 M sodium citrate/0.1% sodium dodecyl sulfate-containing solution at 50° C.); (2) A denaturing agent such as formamide is used during hybridization (e.g., a 42° C. solution containing 50% (v/v) formamide, 0.1% bovine serum albumin/0.1% Ficoll/0.1% polyvinylpyrrolidone/50 mM sodium phosphate buffer at pH 6.5, 750 mM sodium chloride, and 75 mM sodium citrate); or (3)

A filter is incubated overnight at 37° C. in a solution containing 20% formamide, 5×SSC, 50 mM sodium phosphate (pH 7.6), 5×Denhardt's solution, 10% dextran sulfate, and 20 mg/ml denatured sheared salmon sperm DNA. Next, the filter is washed with 1×SSC at about 37 to 50° C. Note that the concentration of formamide may be 50% or more. The washing time may be 5, 15, 30, 60, 120 minutes or longer. A plurality of factors such as a temperature and a salt concentration seem to affect the stringency of a hybridization reaction. The details can be found in Ausubel et al., Current Protocols in Molecular Biology, Wiley Interscience Publishers, (1995).

In addition, the above anti-integrin α8β1 antibodies may contain a heavy chain containing a VH region having heavy chain CDRs 1 to 3 and heavy chain FRs 1 to 4. The heavy chain is encoded by a nucleotide sequence in a plasmid deposited under a deposit number NITE BP-824, NITE BP-826, or NITE BP-828. In addition, the above anti-integrin α8β1 antibodies may contain a light chain containing a VL region having light chain CDRs 1 to 3 and light chain FRs 1 to 4. The light chain is encoded by a nucleotide sequence in a plasmid deposited under a deposit number NITE BP-825, NITE BP-827, or NITE BP-829

In addition, the above anti-integrin α8β1 antibodies can be produced from cells containing a plasmid deposited under a deposit number NITE BP-824, NITE BP-826, or NITE BP-828. Also, these cells may further contain a plasmid deposited under a deposit number NITE BP-825, NITE BP-827, or NITE BP-829.

In addition, the above anti-integrin α8β1 antibodies can be produced from cells containing a vector having a nucleotide sequence encoding a heavy chain or VH of an anti-integrin α8β1 antibody, the nucleotide sequence being encoded by a plasmid deposited under a deposit number NITE BP-824, NITE BP-826, or NITE BP-828. This vector may further contain a nucleotide sequence encoding a light chain or VL of an anti-integrin α8β1 antibody, the nucleotide sequence being encoded by a plasmid deposited under a deposit number NITE BP-825, NITE BP-827, or NITE BP-829. Also, the above cells may further contain a vector having a nucleotide sequence encoding a light chain or VL of an anti-integrin α8β1 antibody, the nucleotide sequence being encoded by a plasmid deposited under a deposit number NITE BP-825, NITE BP-827, or NITE BP-829.

Note that the plasmid of the above deposit number NITE BP-824 has a size of about 6.8 kbp. In this plasmid, the region encoding the heavy chain of the anti-integrin α8β1 antibody has a size of about 1.7 kbp. The regions upstream and downstream of this region encoding the heavy chain of the anti-integrin α8β1 antibody have restriction enzyme sites, KpnI and PinAI, respectively. Accordingly, the plasmid of the deposit number NITE BP-824 can be digested with KpnI and PinAI to isolate a polynucleotide containing the region encoding the heavy chain of the anti-integrin α8β1 antibody. Note that the plasmid of the above deposit number NITE BP-825 has a size of about 6.5 kbp. In this plasmid, the region encoding the light chain of the anti-integrin α8β1 antibody has a size of about 1 kbp. The regions upstream and downstream of this region encoding the light chain of the anti-integrin α8β1 antibody have restriction enzyme sites, HindIII and XbaI, respectively. Accordingly, the plasmid of the deposit number NITE BP-825 can be digested with HindIII and XbaI to isolate a polynucleotide containing the region encoding the light chain of the anti-integrin α8β1 antibody. In addition, a known procedure can be used to isolate a polynucleotide containing a region encoding a heavy chain or a light chain of an antibody from any of the plasmids deposited under the above deposit numbers NITE BP-826 and NITE BP-828 or NITE BP-827 and NITE BP-829.

As used herein, the term "antibody" refers to a molecule which specifically binds to a specific epitope localized on an antigen, and also refers to a population of the molecule. In addition, the term "antibody" may include polyclonal and monoclonal antibodies. In addition, antibodies have a wide variety of forms. Examples may include at least one forms selected from the group consisting of an Fv, Fab, F(ab')$_2$, Fab', diabody, single-chain antibody (e.g., an scFv), dsFv, multivalent antibody (e.g., a divalent antibody), antigen-binding peptide or polypeptide, chimeric antibody (e.g., a mouse-human chimeric antibody), mouse antibody, humanized antibody, human antibody, and equivalent thereof. Also, the antibodies may be or may not be modified. With regard to the modified antibodies, various molecules such as polyethylene glycol may be conjugated to an antibody. With regard to the modified antibodies, an antibody can be chemically modified using a known method.

A polyclonal antibody can be produced by immunizing, for example, a mammal (e.g., a rat, mouse, guinea pig, rabbit, cow, and monkey) or bird with immunogen containing an antigen of interest so as to induce production of an antigen-specific polyclonal antibody. Administration of the immunogen may require coinjection of one or more immunizing agents and an adjuvant as desired. The adjuvant may be used to increase an immune response. The adjuvant may include Freund's adjuvant (complete or incomplete), a mineral gel (e.g., aluminum hydroxide), and/or a surfactant (e.g., lysolecithin). An immunization protocol is publicly known in the art. Any method for inducing an immune response in a selected host organism may be carried out ("Protein Experiment Handbook", YODOSHA CO., LTD. (2003), 86-91).

Except for a small number of antibodies having a naturally occurring mutation, individual antibodies of a monoclonal antibody population may correspond to substantially a single epitope. Also, the individual antibodies of the antibody population may be substantially the same except for a small number of antibodies having a naturally occurring mutation. A monoclonal antibody is highly specific and differs from a regular polyclonal antibody, which typically contains different antibodies binding to different epitopes. In addition to its specificity, the monoclonal antibody is useful in view of synthesizing the antibody by hybridoma culture without contamination of other immunoglobulins. The modifier "monoclonal" may indicate a feature of an antibody which can be obtained from substantially a pure antibody population, but does not mean that the antibody has to be produced by any particular method. For example, the monoclonal antibody described herein may be produced by a method similar to a hybridoma method disclosed in Köhler G and Milstein C, Nature, 1975, Aug. 7, 256 (5517), 495-497. Alternatively, the monoclonal antibody used in embodiments of the present invention may be produced by a method similar to the recombinant technology disclosed in U.S. Pat. No. 4,816,567. In addition, the monoclonal antibody used herein may be isolated from a phage antibody library by a method similar to the technology described in Clackson et al., Nature, 1991, Aug. 15, 352 (6336), 624-628 or Marks et al., J Mol Biol., 1991, Dec. 5, 222(3), 581-597. Furthermore, the antibody may be generated by a procedure disclosed in "Protein Experiment Handbook", YODOSHA CO., LTD., (2003), 92-96.

An Fv is an antibody fragment that contains an antigen recognition site. The Fv consists of a dimer between one heavy chain variable domain and one light chain variable domain, which domains are coupled by non-covalent bonds. Using this structure, three CDRs of the respective variable domains can interact with one another to form an antigen binding site on the surface of the VH-VL dimer.

A Fab is an antibody fragment produced by digesting, for example, an antibody containing Fab regions and an Fc region by a protease papain, the fragment having the N-terminal half of the H chain and the whole L chain linked by a disulfide bond. A Fab can be obtained by digesting, for example, an anti-integrin α8β1 antibody containing Fab regions and an Fc region according to an embodiment of the present invention by a protease papain.

A F(ab')$_2$ is an antibody fragment containing two Fab regions derived from a fragment as produced by digesting, for example, an antibody containing Fab regions and an Fc region by a protease pepsin. A F(ab')$_2$ can be obtained by digesting, for example, an anti-integrin α8β1 antibody containing Fab regions and an Fc region according to an embodiment of the present invention by a protease pepsin. Also, the F(ab')$_2$ can be produced by linking, for example, the following Fab's via a thioether bond or a disulfide bond.

A Fab', for example, is an antibody fragment as produced by cleaving the disulfide bond in the hinge region of a F(ab')$_2$ fragment. The Fab' can be produced by treating the F(ab')$_2$ with a reducing agent such as dithiothreitol.

An scFv is an antibody fragment in which VH and VL are linked via a suitable peptide linker. The scFv can be produced by obtaining cDNAs encoding the VH and VL of an anti-integrin α8β1 antibody according to an embodiment of the present invention, constructing a polynucleotide encoding a VH-peptide linker-VL fragment, cloning the polynucleotide into a vector, and using cells expressing the vector to produce an scFv.

A diabody is an antibody fragment having a divalent antigen-binding activity. Both of the two antigen-binding activities can be identical, or one of them can be a distinct antigen-binding activity. The diabody can be produced by constructing a polynucleotide encoding, for example, scFVs linked using a peptide linker having an amino acid sequence of 8 residues or less, cloning the resulting polynucleotide into a vector, and using cells expressing the vector to produce a diabody.

A dsFv is an antibody fragment in which a VH polypeptide containing a cysteine residue and a VL polypeptide containing a cysteine residue are linked via a disulfide bond between the above cysteine residues. The amino acid residue substituted by the cysteine residue can be selected based on an antibody conformation prediction in accordance with a procedure indicated by Reiter et al. (Reiter et al., Protein Eng., 1994, May, 7(5), 697-704).

An antigen-binding peptide or polypeptide is an antibody fragment containing the VH and/or VL of an antibody or CDRs 1, 2, and/or 3 thereof. A plurality of peptides containing a CDR(s) can be linked directly or indirectly via a suitable peptide linker.

A process for producing the above Fv, Fab, F(ab')$_2$, Fab', scFv, diabody, dsFv, and antigen-binding peptide or polypeptide (hereinafter, sometimes referred to as "Fv etc.") is not particularly limited. For example, the Fv, etc., can be produced by cloning a DNA encoding regions (such as Fv etc.) of an anti-integrin α8β1 antibody according to an embodiment of the present invention into an expression vector and by using cells expressing the vector for their production. In addition, a chemical synthesis process such as an Fmoc (fluorenylmethyloxycarbonyl) process and a tBOC (t-butyloxycarbonyl) process may be used for their production. Note that as used herein, an anti-binding fragment may include at least one of the above Fv, etc.

A chimeric antibody can be typically produced by linking variable regions of an antibody derived from one species to constant regions of an antibody derived from another species, and can be easily constructed using gene recombinant technology. A process for producing a chimeric antibody is known in the art. For example, a mouse-human chimeric antibody can be produced by a process disclosed in Roguska et al., Proc Natl Acad Sci USA., 1994, Feb. 1, 91(3), 969-973. For example, a basic procedure for producing a mouse-human chimeric antibody includes: isolating a mouse leader sequence and a variable region sequence present in a cloned cDNA; and linking these sequences to a sequence encoding a constant region of a human antibody, the sequence being present in a mammalian expression vector. Alternatively, a mouse leader sequence and a variable region sequence present in a cloned cDNA may be first linked to a sequence encoding a constant region of a human antibody and the resulting sequence is then ligated into a mammalian expression vector. A fragment of the constant region of the human antibody can be a constant region of an H chain or a constant region of an L chain of any human antibody. Examples of the constant region of the human H chain can include Cγ1, Cγ2, Cγ3 and Cγ4. Examples of the C region of the L chain can include Cγ and Cκ.

A humanized antibody typically has one or more CDRs derived from a non-human species, human-immunoglobulin-derived framework regions (FRs), and a human-immunoglobulin-derived constant region. The humanized antibody binds to a desired antigen. An antibody can be humanized by using various techniques known in the art (Almagro et al., Front Biosci., 2008, Jan. 1, 13, 1619-1633). Examples of the techniques can include CDR grafting (Ozaki et al., Blood, 1999, Jun. 1, 93(11), 3922-3930), re-surfacing (Roguska et al., Proc Natl Acad Sci USA., 1994, Feb. 1, 91(3), 969-973), and FR shuffling (Damschroder et al., Mol Immunol., 2007, April, 44(11), 3049-3060, Epub 2007, Jan. 22). In order to modify (or, preferably, improve) the antigen binding, amino acid residues in the human FR regions may be substituted by residues corresponding to those of the CDR-donor antibody. This FR substitution can be implemented using a procedure well-known in the art (Riechmann et al., Nature, 1988, Mar. 24; 332(6162): 323-327). For example, the interaction between CDRs and FRs may be simulated to identify FR residues that are critical in antigen binding. Alternatively, their sequences may be compared to identify FR residues that are abnormal at a specific position.

A human antibody typically has a heavy chain variable region and a constant region and a light chain variable region and a constant region, all of which are derived from genes encoding a human immunoglobulin. Examples of a basic method for generating a human antibody include a method using a human-antibody-producing transgenic mouse, phage display, and the like. The method using a human-antibody-producing transgenic mouse includes: introducing a functional human Ig gene into an endogenous-Ig-knockout mouse; and producing, instead of mouse antibodies, human antibodies having versatile antigen-binding abilities. Further, if this mouse is immunized, a human monoclonal antibody can be obtained using a conventional hybridoma procedure. For example, the human antibody can be prepared using a method disclosed in Lonberg et al., Int Rev Immunol., 1995, 13(1), 65-93. The phage display is typically a system in which an exogenous gene is made to be expressed as a fusion protein at an N-terminal portion of a coat protein (e.g., g3p, g10p) of a filamentous phage such as M13 or T7, an *E. coli* virus, without losing infectivity of the phage. For example, the human antibody can be generated using a method disclosed in Vaughan et al., Nat Biotechnol., 1996, Mar., 14(3), 309-314.

In addition, an antibody may be created by grafting (CDR-grafting) heavy chain CDRs or light chain CDRs of an anti-integrin α8β1 antibody according to an embodiment of the present invention into any antibody (Ozaki et al., Blood, 1999, Jun. 1; 93(11): 3922-3930). In addition, an antibody can be obtained by isolating a DNA encoding heavy chain or light chain CDRs of an anti-integrin α8β1 antibody according to an embodiment of the present invention and a DNA encoding regions, other than the heavy chain or light chain CDRs, of a known antibody derived from a human or non-human organism, by ligating these DNAs into a vector in accordance with a procedure known in the art, and then by using known cells to express the vector. At this time, in order to increase efficiency of binding of an anti-integrin α8β1 antibody to a target antigen, it is possible to optimize regions except for the heavy chain CDRs or light chain CDRs by using a process known in the art (e.g., a phage display or a process for screening for an antibody having high reactivity by mutating, at random, amino acid residues of the antibody). In addition, the FR regions may be optimized using, for example, FR shuffling (Damschroder et al., Mol Immunol., 2007, April; 44(11): 3049-3060, Epub 2007, Jan. 22) or a process for substituting amino acid residues within a vernier zone and/or packaging residues (JP2006-241026A or Foote et al., J Mol Biol., 1992, Mar. 20, 224(2), 487-499).

A heavy chain is a main component of a full-length antibody. The heavy chain, in general is linked to a light chain via a disulfide bond and non-covalent bonds. The N-terminal domain of the heavy chain has what is called a variable region (VH) whose amino acid sequence is not the same even in the same class of an antibody derived from the same species. Generally speaking, the VH is known to contribute largely to specificity and affinity to an antigen. An article (Reiter et al., J Mol Biol., 1999, Jul. 16; 290(3): 685-98), for example, has reported that a molecule containing only a VH was able to bind to an antigen with high specificity and affinity. Further, an article (Wolfson W, Chem Biol., 2006, December; 13(12): 1243-1244) has reported that among camel antibodies is an antibody having only a heavy chain without a light chain.

In an antibody, CDRs (complementarity determining regions) are regions which actually and directly contact an antigen to form a binding site. Generally speaking, the CDRs are localized in the Fv (a variable member including a heavy chain variable region (VH) and a light chain variable region (VL) of an antibody. Also, the CDRs, in general, include CDR1, CDR2, and CDR3 having about 5 to 25 amino acid residues. Here, the heavy chain CDRs, in particular, are known to contribute to binding of an antibody to an antigen. Among the CDRs, CDR3 is known to contribute most to the binding of an antibody to an antigen. An article (Willy et al., Biochemical and Biophysical Research Communications Volume 356, Issue 1, 27, April 2007, Pages 124-128), for example, discloses that modification of the heavy chain CDR3 increased the binding ability of an antibody. In addition, the CDRs determine the specificity of an antibody against an antigen. Accordingly, the regions largely vary in their amino acid sequences between antibodies, and are also called a hypervariable region. Fv regions other than the CDRs are called framework regions (FR). The FR regions include FR1, FR2, FR3, and FR4 and are relatively well conserved (Kabat et al., "Sequence of Proteins of Immunological Interest" US Dept. Health and Human Services, 1983). That is, characteristics of the antibody reactivity are said to be first determined by the heavy chain CDR3 and next determined by the heavy chain CDRs.

Several reports have disclosed CDR definitions and methods for determining a CDR position. For example, Kabat's definition (Sequences of Proteins of Immunological Interest, 5th ed., Public Health Service, National Institutes of Health, Bethesda, Md. (1991)) or Chothia's definition (Chothia et al., J. Mol. Biol., 1987; 196: 901-917) may be used. In the text of specification of the present application, the Kabat's definition is used as a preferable definition. The definition, however, is not limited to the above. In addition, the CDRs may be determined by considering both the Kabat's definition and the Chothia's definition. For example, a portion in which the CDRs defined by both definitions overlap may be determined as a CDR. Alternatively, a portion containing both the CDRs defined by the two definitions may be determined as a CDR. Specific examples of such a method include Martin's method using Oxford Molecular's AbM antibody modeling software (Proc. Natl. Acad. Sci. USA, 1989; 86: 9268-9272), a proposal in which the Kabat's definition and the Chothia's definition are compromised.

As used herein, examples of the anti-fibrosis agent include a drug for suppressing fibrosis. Also, the examples include a drug for a disease accompanied by progression of fibrosis. In addition, the anti-fibrosis agent may be a fibrosis-suppressing agent used for regenerative medicine. Note that as used herein, the term "treatment" refers to exerting a prophylactic effect or a symptom-improving effect on a disease (including fibrosis) of a subject or on one or more symptoms involving the disease. Examples of the drug include a prophylactic.

Further, the anti-fibrosis agent may be a pharmaceutical composition containing at least one pharmacologically acceptable carrier. The pharmaceutical composition can be produced by any process known in the technical field of drug formulation. Examples of the process include: mixing an active ingredient with the above carrier. Furthermore, in the anti-fibrosis agent, an active ingredient may be used singly, or may be mixed with any component. Moreover, the dosage form of the above carrier is not particularly limited.

An administration route effective in treatment is preferably used. Examples of the administration route include intravenous, subcutaneous, intramuscular, intraperitoneal, and oral administration. Examples of a dosage form may include an injection, a capsule, a tablet, and granules. When an antibody medicine is administered, use of an injection is effective. An aqueous solution for an injection may be stored in, for example, a vial or a stainless container. In addition, the aqueous solution for an injection may be combined with, for example, a saline solution, sugar (e.g., trehalose), NaCl, or NaOH. Further, the anti-fibrosis agent may be combined with, for example, a buffer (e.g., a phosphate buffer) and/or a stabilizer.

A dosage is not particularly limited, but may be, for example, 0.25 or 0.5 mg/body weight per administration. The dosage may be between the above values. An administration interval is not particularly limited, but may be, for example, every 3 days for 2 weeks. The agent may be administered twice a week for 4 weeks. In addition, the dosage, the administration interval and the administration method can be appropriately selected depending on the age, weight, symptom, affected organ, etc., of a subject. In addition, the administration may be combined with a suitable chemotherapeutic agent. Further, the anti-fibrosis agent preferably contains an effective dose of active ingredient, the amount of which is effective in exerting a desired effect. The same administration method as for the anti-fibrosis agent preferably applies to the above collagen accumulation inhibitor, collagen aα1(I) and α-SMA expression inhibitor, and hydroxyproline production inhibitor.

As used herein, examples of the subject include a human and non-human mammals (e.g., at least one of a mouse, guinea pig, hamster, rat, rodent, rabbit, pig, sheep, goat, cow, horse, cat, dog, marmoset, monkey, and chimpanzee).

As used herein, the term "or" may be used when "at least one" matter listed in the text of specification can be employed. The same applies to the term "in addition". As used herein, when the term "between any two of the above values" is indicated, the two values are inclusive in the range.

As described above, the embodiments of the present invention have been illustrated. These embodiments are examples of the present invention. Accordingly, various configurations other than the above embodiments can be adopted. In addition, combinations among the above-described embodiments can also be employed.

EXAMPLES

Hereinafter, the present invention is further illustrated by referring to Examples. The present invention, however, is not limited to them.

<Example 1> Generation of Anti-Integrin α8β1 Antibody (1) Immunization

A cDNA encoding the mouse integrin α8 chain was cloned into a mammalian expression vector. Next, the expression vector was transfected into a chicken lymphoblastoid cell line by electroporation. Then, an antibiotic was added, and vector-expressing cells were selected. A chicken was hyperimmunized with the resulting mouse integrin α8-expressing cells. An antibody titer in the chicken serum was determined by flow cytometry (FACS) analysis. The FACS analysis was performed in accordance with a typical protocol of FACSCalibur (BD, USA).

Note that it was verified that integrin α8 and β1 chains form a heterodimer in any of birds and mammals (Bossy B et al., EMBO J, 10(9): 2375-2385, 1991; J Cell Sci, 108: 537-544, 1995). In this regard, however, specific experimental data on whether or not a mammalian a chain and a bird β chain can form a heterodimer have not been published. In view of this situation, the following procedure was used to verify whether or not the human α9 chain and the chicken β1 chain form a heterodimer and the heterodimer is expressed on the plasma membrane. First, a cDNA encoding the human α9 chain was introduced into a chicken cell line. Next, the cell line was subjected to drug selection, and a stable cell line was established. Then, this human α9-expressing chicken cell line was lysed using a detergent, and the lysate was subjected to coimmunoprecipitation using an anti-human integrin α9 antibody Y9A2 (see FIG. 1). The lane 1 had two bands, which indicated formation of a complex between the human α9 chain and another molecule. The lane 2 shows the result of coimmunoprecipitation using the lysate of integrin α9β1-expressing α9-transfected SW480 cells (a human colon cancer cell line). When the lanes 1 and 2 are compared, the two bands in the lane 1 are shown to be α9 and β1 chains.

Figure 2:
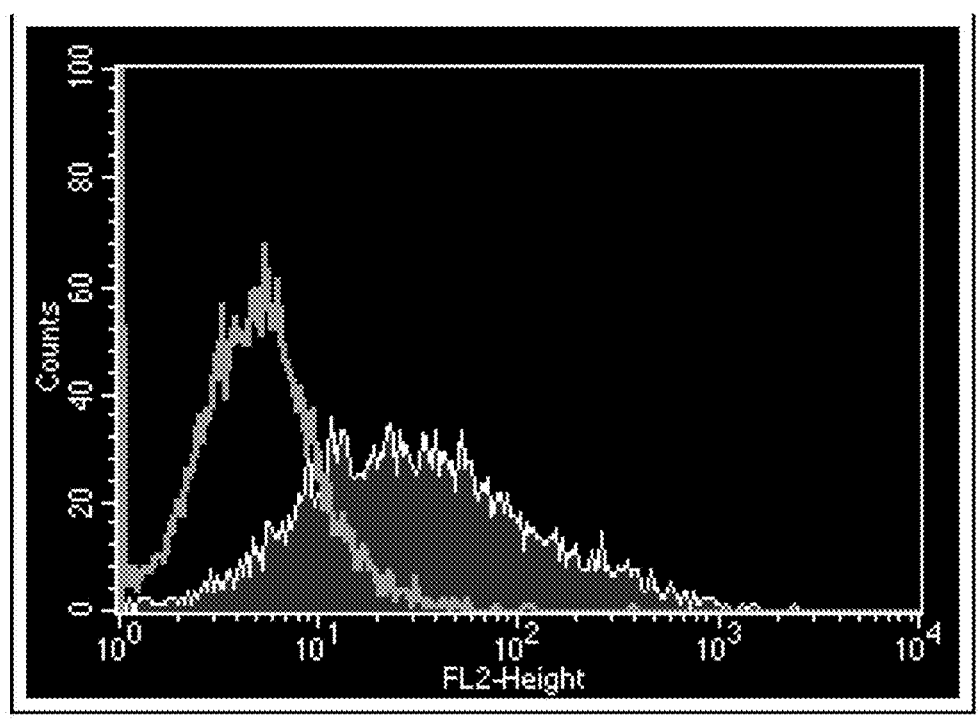
FIG. 2 shows the results of FACS analysis using an anti-human integrin α9 antibody Y9A2 and a human integrin α9-introduced chicken cell line.

Further, FACS analysis was conducted using the anti-human integrin α9 antibody Y9A2 and the human integrin α9-introduced chicken cell line (FIG. 2). When the histogram of stain-free cells was compared with that of antibody-stained cells, the latter histogram was shifted toward the right direction. This demonstrated expression of the human α9 chain on the plasma membrane. In view of this, the α8 and β1 chains seem to form a heterodimer on the surface of the above integrin α8 chain-expressing cell line. Note that the amino acid sequence of the above human integrin α8 chain is the amino acid sequence set forth in SEQ ID NO: 7.

(2) Generation of scFv Phage Antibody Library

First, a spleen was excised from the immunized chicken. Next, lymphocytes were isolated. RNA was extracted from the lymphocytes obtained. Then, cDNA was synthesized and an scFv phage antibody library was constructed. The phage antibody library was constructed in accordance with a typical procedure described in Nakamura et al., J Vet Med Sci., 2004, July, 66(7), 807-14.

(3) Panning

The scFv phage antibody library was added to mouse integrin α8 expression-free cells, and non-specific phages were adsorbed. Next, the resulting library was reacted with the mouse integrin α8-expressing cells. The mixture was washed with an organic solvent. Then, phages which had bound to the mouse integrin α8-expressing cells were collected, and Escherichia coli bacteria were infected therewith. After panning was performed four times, the library reactivity was examined by FACS analysis using the mouse integrin α8-expressing cells. Since the third library had high reactivity, phages were cloned from the third library. After selection of positive clones, their sequences were determined. The cell panning was performed according to a procedure described in Giordano et al., Nat Med., 2001, November, 7(11), 1249-53.

(4) Selection of Clones Cross-reacted with Human Integrin α8 Chain

In order to obtain an antibody which was able to cross-react with the human integrin α8 chain, a human integrin α8-expressing chicken lymphoblastoid cell line was produced. Clones which had cross-reacted with the human integrin α8-expressing cell line were selected by FACS.

(5) Engineering of Recombinant IgY (rIgY) Antibody

A DNA strand encoding each scFv phage antibody as obtained in the above experiments was used as a template to perform a PCR to amplify its VH and VL. Next, an overlap PCR using primers of the leader sequence and constant regions of a chicken antibody was carried out to clone the fragments into rIgY expression vectors. Then, the prepared H-chain and L-chain constructs were transfected into mammalian cultured cells. After that, an expressed antibody protein was purified. Engineering of the rIgY antibody was performed in accordance with a typical procedure described in Shimamoto et al., Biologicals, 2005, September, 33(3), 169-74. The above procedure was used to prepare three anti-integrin α8β1 antibodies (monoclonal antibodies) (the #3 antibody, #5 antibody, and #26 antibody).

Respective plasmids containing a DNA sequence encoding a heavy chain of the #3, #5, or #26 antibody were domestically deposited at Biological Resource Center, National Institute of Technology and Evaluation (Kazusa Kamatari 2-5-8, Kisarazu-city, Chiba) on Oct. 16, 2009. After that, the above domestically deposited plasmids were changed to international deposition on Oct. 12, 2010, as Accession No: NITE BP-824, Accession No: NITE BP-826, and Accession No: NITE BP-828, respectively, under the Budapest Treaty.

Respective plasmids containing a DNA sequence encoding a light chain of the #3, #5, or #26 antibody were domestically deposited at Biological Resource Center, National Institute of Technology and Evaluation on Oct. 16, 2009. After that, the above domestically deposited plasmids were changed to international deposition on Oct. 12, 2010, as Accession No: NITE BP-825, Accession No: NITE BP-827, and Accession No: NITE BP-829, respectively, under the Budapest Treaty. Those six deposited plasmids were constructed using the same expression vector as in the above section (5).

In addition, the heavy chain CDRs 1, 2, and 3 of the #3 antibody have amino acid sequences of SYDMV (SEQ ID NO: 1), IYSAGSGPQYAPAVKG (SEQ ID NO: 2), and ADSTYCASGSCYAADSID (SEQ ID NO: 3), respectively. Also, the light chain CDRs 1, 2, and 3 of the #3 antibody have amino acid sequences of SGGGSWYG (SEQ ID NO: 4), DNTNRPS (SEQ ID NO: 5), and GSADSTDAV (SEQ ID NO: 6), respectively. The CDRs are sites that are involved in the antigen-binding specificity of an anti-integrin α8β1 antibody. In addition, the heavy chain CDRs 1, 2, and 3 of the #5 antibody have amino acid sequences of SYDMA (SEQ ID NO: 10), IDDDDSFTLYGAAVKG (SEQ ID NO: 11), VGDGYCGWSACGGSID (SEQ ID NO: 12), respectively. Also, the light chain CDRs 1, 2, and 3 of the #5 antibody have amino acid sequences of SGDESYYG (SEQ ID NO: 13), SNDKRPS (SEQ ID NO: 14), GXYDSSTYAGI (SEQ ID NO: 15), respectively. In addition, the heavy chain CDRs 1, 2, and 3 of the #26 antibody have amino acid sequences of GHDMA (SEQ ID NO: 16), IGSSGSNTNYGTAVKG (SEQ ID NO: 17), PGSCYGCTPDAGEID (SEQ ID NO: 18), respectively. Also, the light chain CDRs 1, 2, and 3 of the #26 antibody have amino acid sequences of SGSSGSYYG (SEQ ID NO: 19), ESTKRPS (SEQ ID NO: 20), GNEDSSYVGI (SEQ ID NO: 21), respectively. Note that the "X" denotes an amino acid which was unable to be analyzed by amino acid analysis.

<Example 2> Epitope Evaluation

First, cDNAs encoding 8 different human α8 chains (R120, K125, S132, P161, Y199, A238, A260, and 5261) were constructed. Next, these cDNAs were each transiently expressed on CHO cells and the CHO cells were reacted with the #3 antibody. The #3 antibody was reacted with the wild-type and 7 mutants (K125, S132, P161, Y199, A238, A260, and S261), but was not reacted with the R120 mutant. FIG. 3 shows the results of FACS analysis in which the #3 antibody was reacted with the wild-type, R120 mutant, or P161 mutant. Then, in order to exclude the possibility that the R120K mutant was insufficiently expressed due to its transient expression, a stable cell line was established and the antibody was likewise reacted with the mutant. The reactivity was still not observed. In addition, the R120K mutant was well reacted with a control anti-α8 antibody. This result verified that the R120K mutant was sufficiently expressed (FIG. 4). The above results indicate that an epitope recognized by the #3 antibody is localized to R120 and a periphery thereof.

<Example 3> Evaluation of Blocking Activity Toward Integrin α8β1

Figure 5:
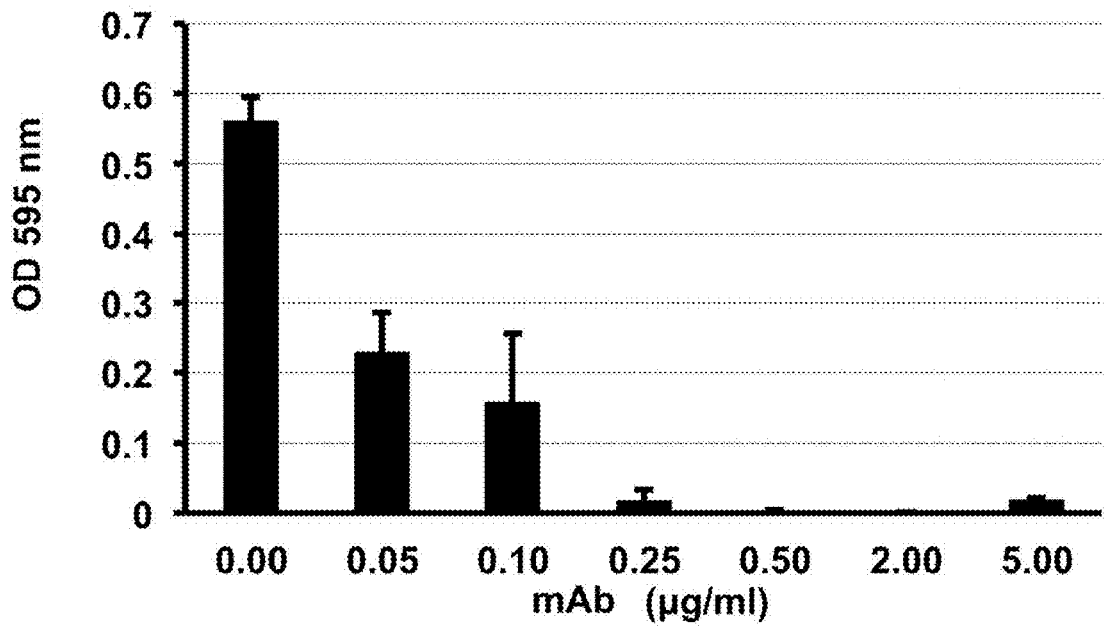
FIG. 5 shows the results of measuring the integrin α8β1 blocking activity of an anti-integrin α8β1 antibody according to an Example.

First, mouse osteopontin (2.5 mg/ml) was immobilized on a 96-well plate. Next, α8-expressing K562 cells were added at 1×10 E5 cells/well to the plate, and the #3 antibody was also added at concentrations designated in FIG. 5. In FIG. 5, absorbance of adherent cells was detected at 570 (A570) nm A lower value at A570 nm indicates less binding between the α8-expressing K562 cells and osteopontin.

These results demonstrated that the #3 antibody blocked the binding between the α8-expressing K562 cells and osteopontin (FIG. 5). That is, the #3 antibody functioned as an antagonist for integrin α8131. In addition, when the value in the case of no antibody addition was set to 100, 60% or higher blocking activity was observed at an antibody concentration of 0.05 μg/ml. Further, 70% or higher blocking activity was observed at an antibody concentration of 0.10 μg/ml and 95% or higher blocking activity was observed at an antibody concentration of 0.25 μg/ml.

<Example 4> Cross-Reactivity Evaluation (1) Evaluation of Cross-Reactivity to Human and Mouse Integrins α8β1

Figure 6:
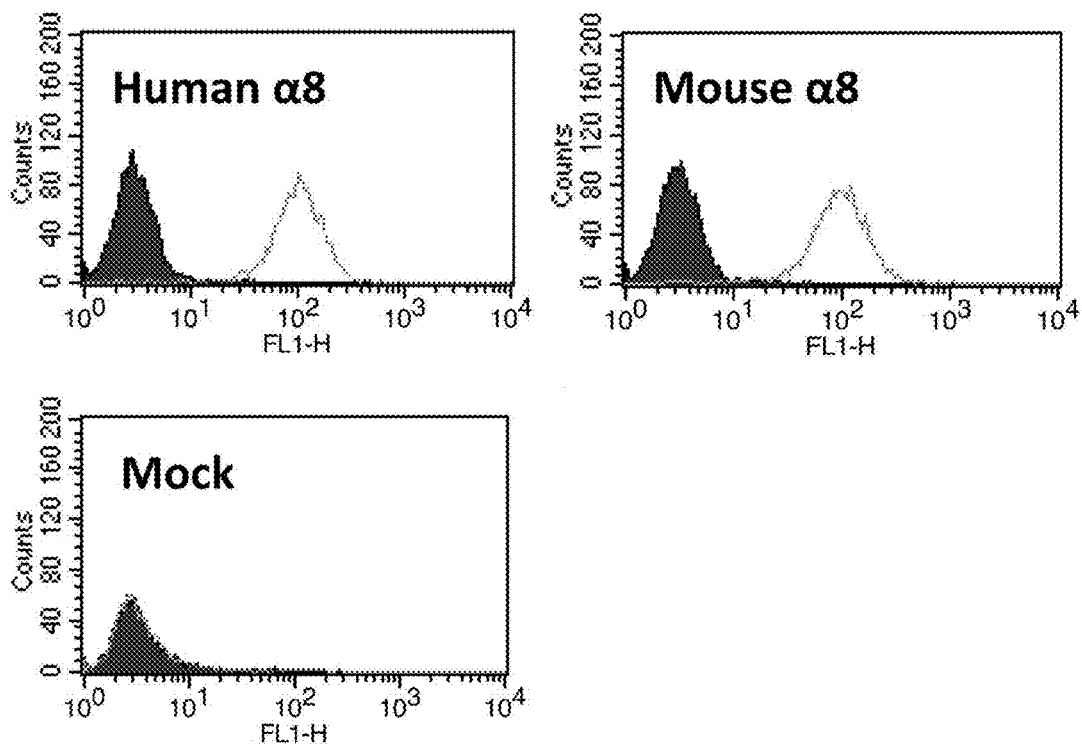
FIG. 6 shows the results of FACS analysis of an anti-integrin α8β1 antibody according to an Example regarding cross-reactivity to integrins α8β1 derived from a human and a mouse.

FACS analysis using the #3 antibody was used to investigate cross-reactivity to a human integrin α8 chain-expressing SW480 cell line and a mouse integrin α8 chain-expressing SW480 cell line. FIG. 6 shows the results. Both the human integrin α8 chain-expressing SW480 cell line and the mouse integrin α8 chain-expressing SW480 cell line were used for experiments. When the #3 antibody was reacted with each cell line, a peak position was clearly shifted in the right direction, compared with that when no antibody was reacted. In addition, no peak shift was observed in the case of mock cells. This demonstrates that the #3 antibody can bind to integrins α8β1 derived from both a human and a mouse.

(2) Evaluation of Cross-Reactivity to Rat Integrin α8β1

First, a cDNA encoding the rat integrin α8 chain was cloned and transiently expressed on CHO cells. The reactivity of the #3 antibody toward the cells was examined by FACS analysis. Cells transiently expressing the human integrin α8 subunit were used as a positive control. FIG. 7 shows that the #3 antibody reacted with the rat integrin α8 chain. The reactivity was substantially the same as in the case of reacting the antibody with the human integrin α8 chain.

(3) Evaluation of Reactivity to Integrins α8β1 Derived from Other Organisms

The results of the above Example 2 indicate that an epitope recognized by the #3 antibody is localized to R120 and a periphery thereof. The amino acid sequence of this region in a rat was searched, and was found to be identical to that of a mouse and a human. Then, the sequences of other species were also collected from databases and were subjected to alignment (FIG. 8). As a result, in a cow, pig, dog, hamster, marmoset, rhesus monkey, gibbon, and chimpanzee, a total of 13 residues (TNNRKIRVNGTKE; SEQ ID NO: 9) including N-terminal 6 residues and C-terminal 6 residues of R120 were 100% matched. Accordingly, the #3 antibody is considered to react with integrin α8β1 derived from any of a hamster, cow, pig, dog, marmoset, rhesus monkey, gibbon, and chimpanzee.

Figure 9:
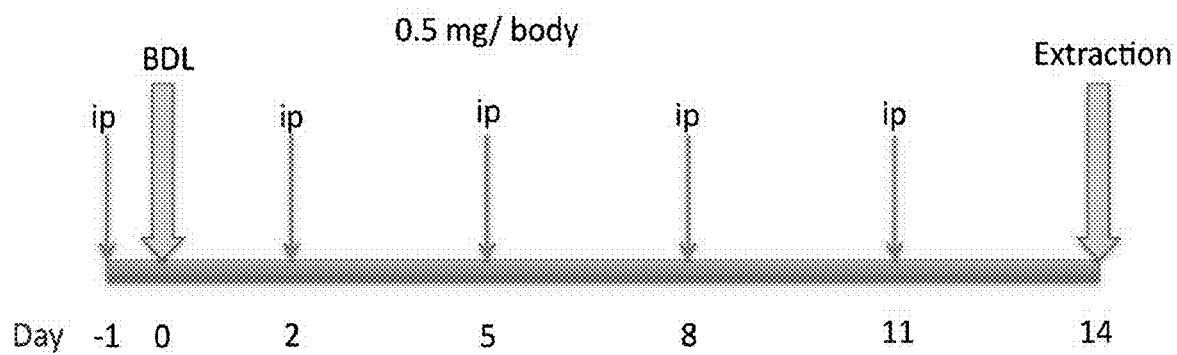
FIG. 9 illustrates a dosage schedule in which an anti-integrin α8β1 antibody according to an Example is administered to a BDL mouse.

<Example 5> Evaluation of Therapeutic Effects by Using Bile Duct Ligation (BDL) Fibrosis Model Mouse (1) Administration to BDL Mouse As illustrated in FIG. 9, the biliary ducts of mice were ligated at Day 0 so as to induce liver fibrosis. By doing so, what is called BDL mice having fibrosis around the biliary ducts in the liver was created. In addition, the endotoxin-free #3 antibody was intraperitoneally administered at 0.5 mg/body weight to the mice every 3 days for 2 weeks. For comparison, the BDL mice without the anti-integrin α8β1 antibody administration were also prepared. Further, the following testes were carried out to determine fibrosis indexes.

(2) Masson's Trichrome Staining

In order to examine fibrosis in a liver tissue of the BDL mice, Masson's trichrome staining was carried out. FIG. 10 shows tissue images around a biliary triad containing a biliary duct, a portal vein, and a hepatic artery. The upper panel shows the case without the #3 antibody administration. In the upper panel, an amount of collagen fiber, which was stained blue, increased, and newly formed small biliary ducts were recognized. This indicated an increase in biliary duct formation. In addition, the epithelium proliferated around a relatively large biliary duct and inflammatory cells infiltrated in a periphery of the biliary duct. Hepatic parenchymal cells were stained red. The lower panel shows the case with the #3 antibody administration. When compared with the upper panel, the lower panel likewise indicated an increase in formation of small biliary ducts, but demonstrated that the levels of increase in an amount of collagen fiber were markedly low. The bile duct ligation caused an internal pressure of the biliary duct to increase, thereby promoting formation of biliary ducts. However, fibrosis accompanied by the phenomenon was found to be suppressed by the antibody administration.

(3) Measuring Levels of Col α1(I) and α-SMA Gene Expressions

Figure 11:
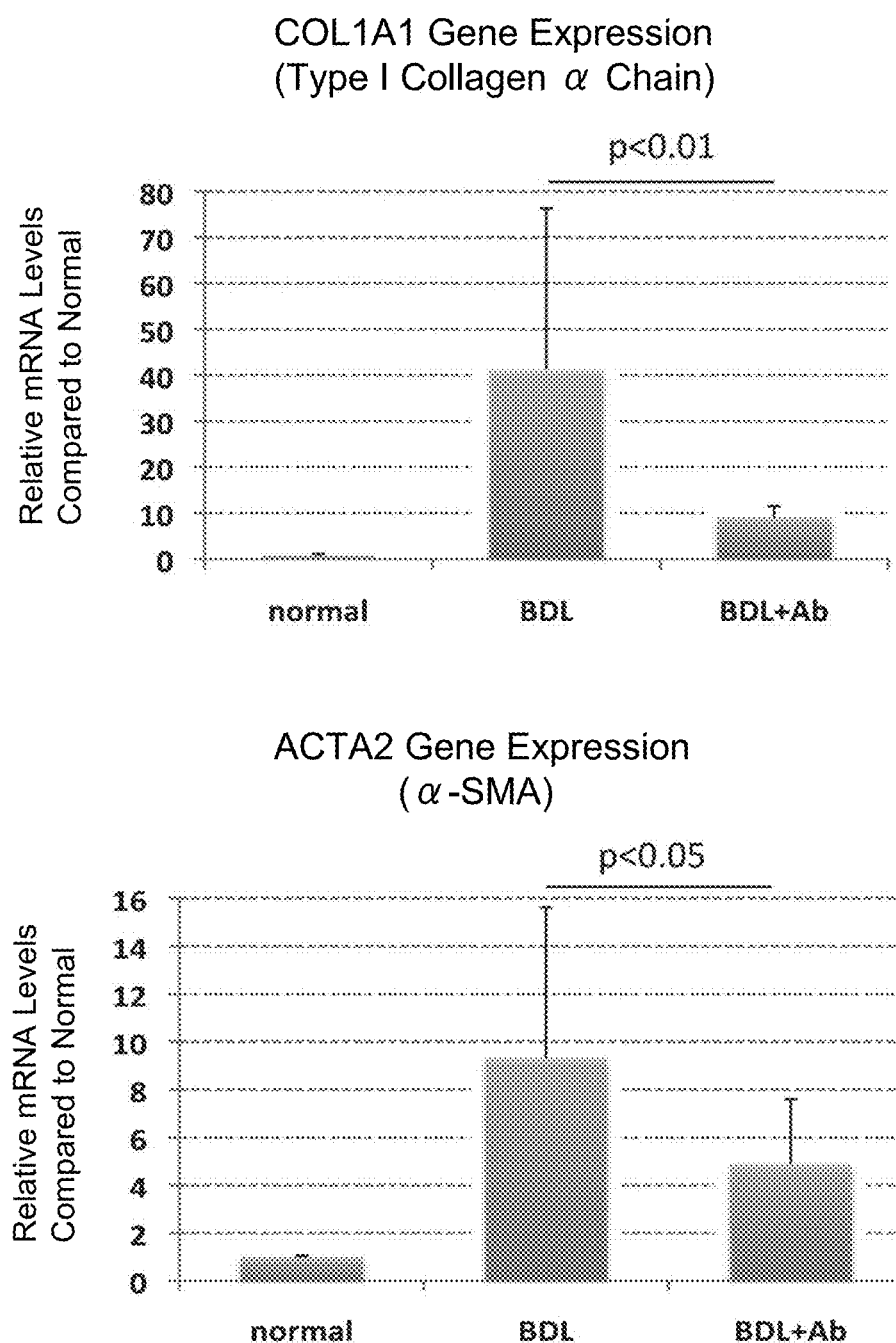
FIG. 11 is graphs illustrating the results of measuring levels of expression of Col α1(I) and α-SMA genes in the livers of BDL mice when an anti-integrin α8β1 antibody according to an Example was or was not administered.

A quantitative PCR method was used to analyze levels of collagen a1 (Col α1(I)) and α-smooth muscle actin (α-SMA) gene expressions in the livers of the BDL mice. Then, the results were compared between the case with the #3 antibody administration and the case without antibody administration. FIG. 11 shows relative expression levels when the levels of normal mice were set to 1.

The levels of Col α1(I) expression in the BDL mice were increased 40 times or more than those of the normal mice. These levels were decreased by the #3 antibody administration to a level that was 10 times or less than those of the normal mice. That is, the #3 antibody administration inhibited the levels of Col α1(I) expression in the BDL mice by 75% or higher. In addition, the levels of α-SMA expression in the BDL mice were increased about 9 times or more than those of the normal mice. These levels were decreased by the #3 antibody administration to a level that was 5 times or less than those of the normal mice. That is, the #3 antibody administration inhibited the levels of expression in the BDL mice by about 50%.

(4) Quantification of Hydroxyproline

Figure 12:
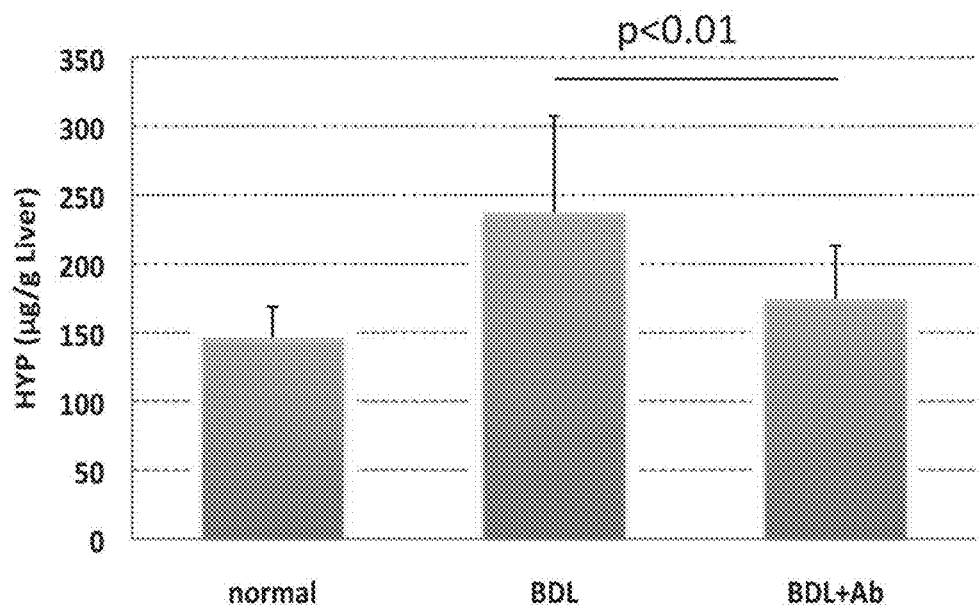
FIG. 12 is a graph illustrating the results of measuring hydroxyproline content in the livers of BDL mice when an anti-integrin α8β1 antibody according to an Example was or was not administered.

Hydroxyproline content reflects an amount of collagen in a tissue and has been used for a standard method for fibrosis quantification. The hydroxyproline content in the liver of each BDL mouse was compared between mice with the #3 antibody administration and mice without antibody administration. FIG. 12 shows the results. The #3 antibody administration reduced the content of hydroxyproline in the BDL mice from 240 μg/g liver tissue to 150 μg/g liver tissue.

Note that, the content of hydroxyproline was measured using the following procedure. First, a mouse liver tissue was homogenized in 6 N HCl to have a concentration of 100 mg/ml. Next, the homogenate was kept at 110° C. for 24 hours without shaking, and was then centrifuged at 800×g for 15 mM to recover a supernatant. Then, 14 μl of 8N NaOH was added to 20 μl of the supernatant to neutralize it. Subsequently, 266 μl of $dH_2O$ was added to the mixture to have a total volume of 0.3 ml. Further, an equal volume of isopropanol was mixed therewith, and 0.1 ml of a chloramine T solution was further added. After the resulting mixture was left at room temperature for 10 mM, 0.5 ml of a dimethylaminobenzaldehyde solution was added and mixed. This mixture was spun down. Then, a coloring reaction was performed at 50° C. for 90 mM After that, the mixture was cooled down at room temperature for 5 mM and 150 μl of the mixture was dispensed on a plate to determine the absorbance at 590 nm (A590). Also, a standard curve as obtained using a standard was used for quantification. Note that used was a chloramine T solution in which 0.336 g of chloramine T (final 0.84%), 0.56 ml of 3 M NaOAc (final 42 mM), 0.02 g of citric acid (final 2.6 mM), and 15.8 ml of isopropanol (final 39.5%) were included and a total volume was adjusted with $dH_2O$ to 40 ml. Also, used was a dimethylbenzaldehyde solution in which 0.248 g of p-dimethylaminobenzaldehyde, 0.27 ml of perchloric acid (60%) and 0.73 ml of isopropanol were mixed.

<Example 6> Evaluation of Therapeutic Effects by Using Carbon Tetrachloride-induced Fibrosis Model Mouse ($CCl_4$ Mouse)

(1) Administration to $CCl_4$ Mouse

Figure 13:
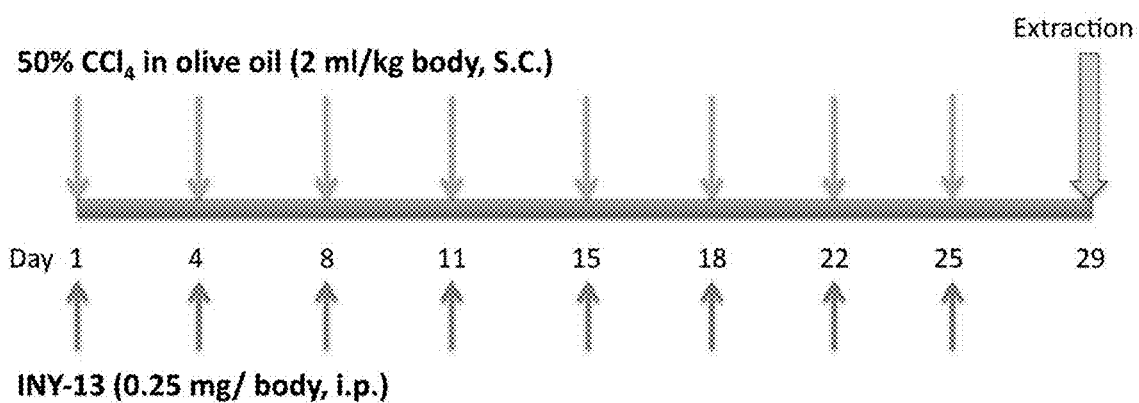
FIG. 13 illustrates a dosage schedule in which an anti-integrin α8β1 antibody according to an Example is administered to a $CCl_4$ mouse.

In order to induce liver fibrosis as illustrated in FIG. 13, 50% carbon tetrachloride as prepared using olive oil as a solvent was subcutaneously administered at 2 ml/kg body weight at Day 1 to mice to create $CCl_4$ mice. In addition, the endotoxin-free #3 antibody was intraperitoneally administered at 0.25 mg/body weight to the mice twice a week for 4 weeks. For comparison, the $CCl_4$ mice without the anti-integrin α8β1 antibody administration were also prepared. Further, the following testes were carried out to determine fibrosis indexes.

(2) Masson's Trichrome Staining

Figure 14:
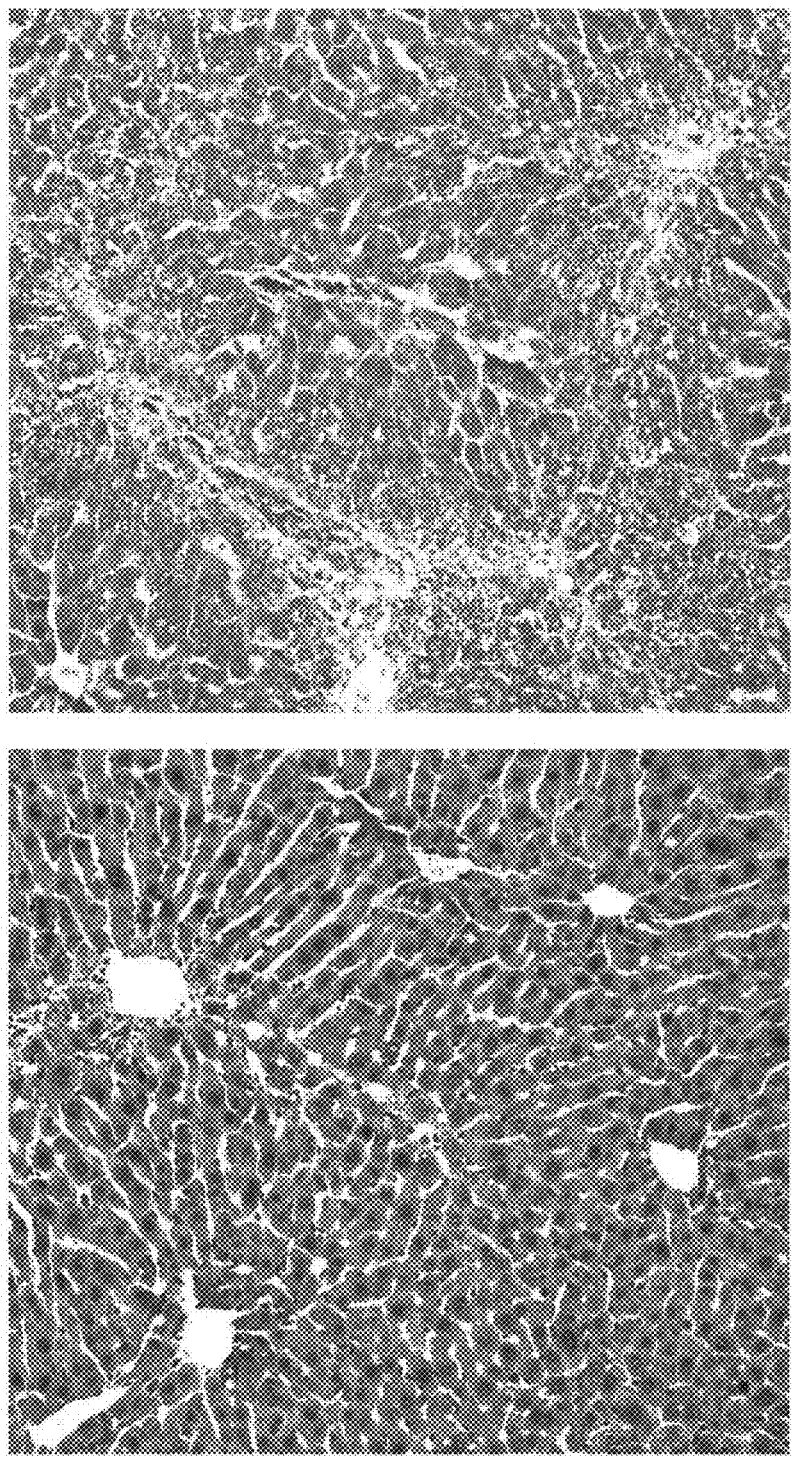
FIG. 14 is photographs of Masson's trichrome staining of liver sections of $CCl_4$ mice when an anti-integrin α8β1 antibody according to an Example was or was not administered.

Liver sections of the $CCl_4$ mice were subjected to Masson's trichrome staining. FIG. 14 shows the results. The upper panel shows the case without the #3 antibody administration. The upper panel shows collagen thickening in a Grisson's capsule around a hepatic lobule. Collagen fibers were stained blue and were thickened like a hexagonal shape on the structure of the hepatic lobule. The lower panel shows the case with the #3 antibody administration. In the lower panel, almost no thickening of a Grisson's capsule around a hepatic lobule as seen in the upper panel was observed.

(3) Levels of α-SMA Expression

Figure 15:
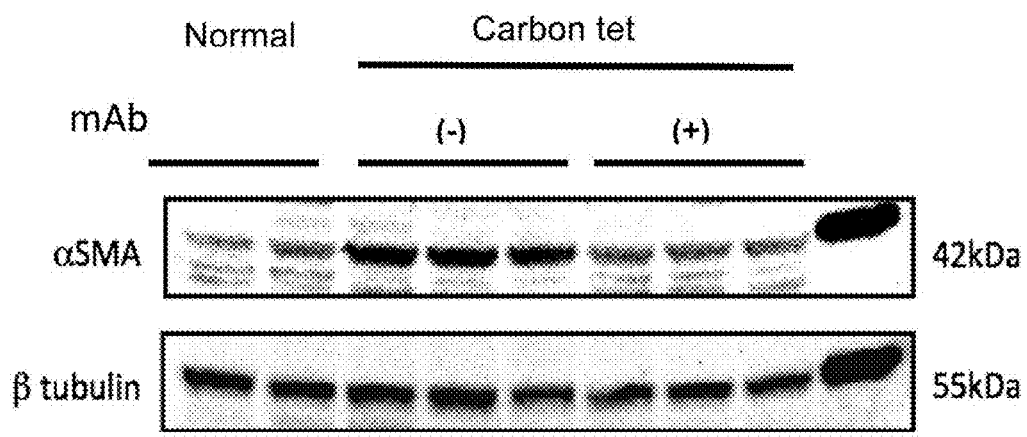
FIG. 15 is images illustrating the results of measuring levels of expression of α-SMA protein in the livers of $CCl_4$ mice when an anti-integrin α8β1 antibody according to an Example was or was not administered.

Western blotting was used to examine the levels of α-SMA protein expression in the livers of normal mice and the $CCl_4$ mice with or without the #3 antibody administration. FIG. 15 shows the results. When the #3 antibody was not administered, the $CCl_4$ mice had higher levels of α-SMA protein expression (mAb (−); n=3) than those in the normal mouse. Meanwhile, the anti-integrin α8β1 antibody administration reduced levels of α-SMA expression (mAb (+); n=3). The lane at the right end represents a positive control (extract of LX2 cells).

(4) Quantification of Hydroxyproline

Figure 16:
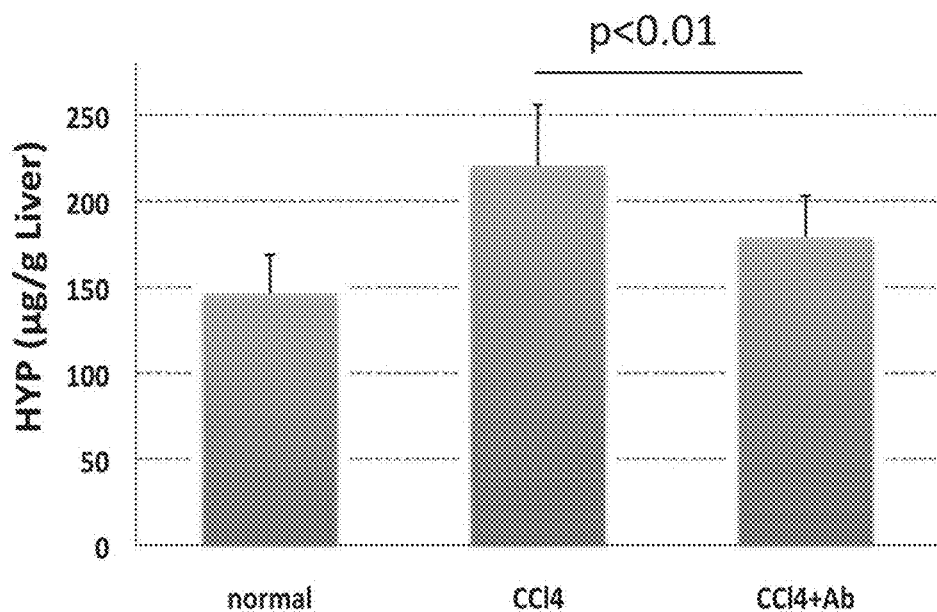
FIG. 16 is a graph illustrating the results of measuring hydroxyproline content in the livers of $CCl_4$ mice when an anti-integrin α8β1 antibody according to an Example was or was not administered.

The hydroxyproline content in the liver of each $CCl_4$ mouse was compared between the mice with the #3 antibody administration and the mice without antibody administration. FIG. 16 shows the results. The #3 antibody administration reduced the content of hydroxyproline in the $CCl_4$ mice from 220 μg/g liver tissue to 177 μg/g liver tissue.

The above results of Examples 5 and 6 have demonstrated that use of the #3 antibody can 1) improve pathohistological findings of fibrosis in liver fibrosis model mice; 2) reduce an increase in levels of collagen α1(I) and α-SMA gene expressions; and 3) reduce an increase in hydroxyproline content. In this way, it was surprising that pathohistological findings were clearly changed in animals. This fact was supported by the numerical values as obtained by quantifying molecules produced during fibrosis formation.

<Example 7> Evaluation of Therapeutic Effects by Using Bleomycin-induced Pulmonary Fibrosis Model Mouse (Pulmonary Fibrosis Mouse)

(1) Administration to Pulmonary Fibrosis Mouse

Figure 17:
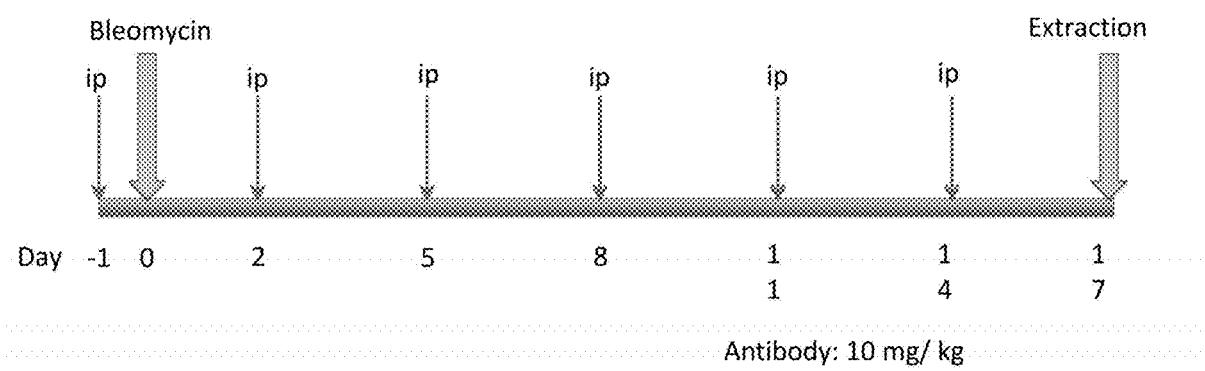
FIG. 17 illustrates a dosage schedule in which an anti-integrin α8β1 antibody according to an Example is administered to a pulmonary fibrosis model mouse.

In order to induce pulmonary fibrosis as illustrated in FIG. 17, bleomycin (NIPPON KAYAKU Co., Ltd.) was intratracheally administered at 1.25 U/kg body weight at Day 0 to mice to create bleomycin-induced pulmonary fibrosis model mice. In addition, the endotoxin-free #3 antibody was intraperitoneally administered at 10 mg/body weight to the mice every 3 days for 2 weeks. As a control, a saline solution was intraperitoneally administered to the bleomycin-induced pulmonary fibrosis model mice for comparison. Further, the following testes were carried out to determine fibrosis indexes.

(2) Pathological Images

Figure 18:
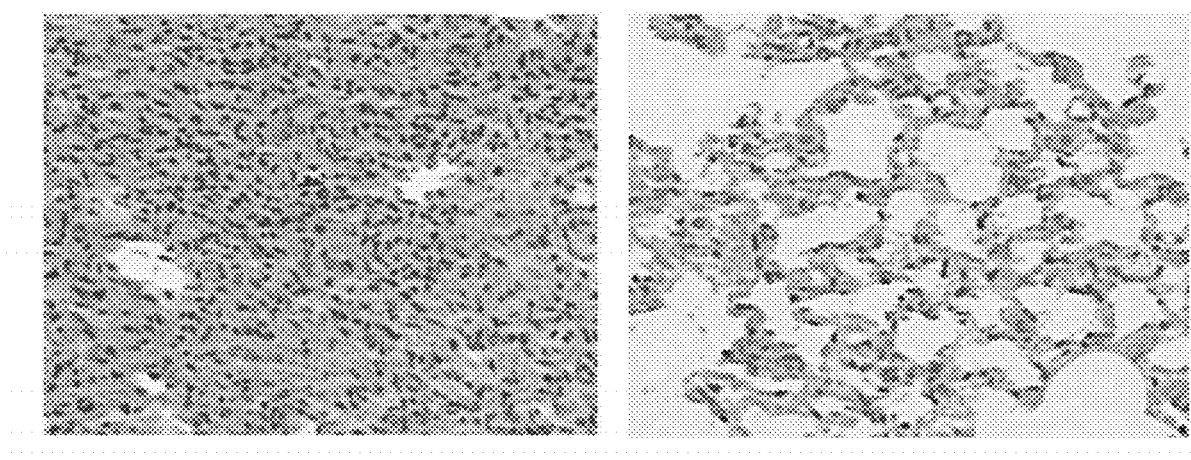
FIG. 18 is photographs of HE staining of lung sections of pulmonary fibrosis model mice when an anti-integrin α8β1 antibody according to an Example was or was not administered.

FIG. 18 shows pathological images (HE staining) of the bleomycin-induced pulmonary fibrosis mice at 21 days after the bleomycin administration. The left image shows that a control group mouse had severe fibrosis. Inflammatory cells infiltrated; the number of fibroblasts increased; and fiber deposition occurred. These phenomena indicated loss of the normal structure of pulmonary alveoli. By contrast, the right image shows that the lung of an antibody administration group mouse had more thickening of alveolar septum and more infiltration of inflammatory cells than a normal lung. However, the structure of pulmonary alveoli remained and fibrosis was strongly inhibited compared with the control group.

(3) Time Course of Body Weight Changes

Figure 20:
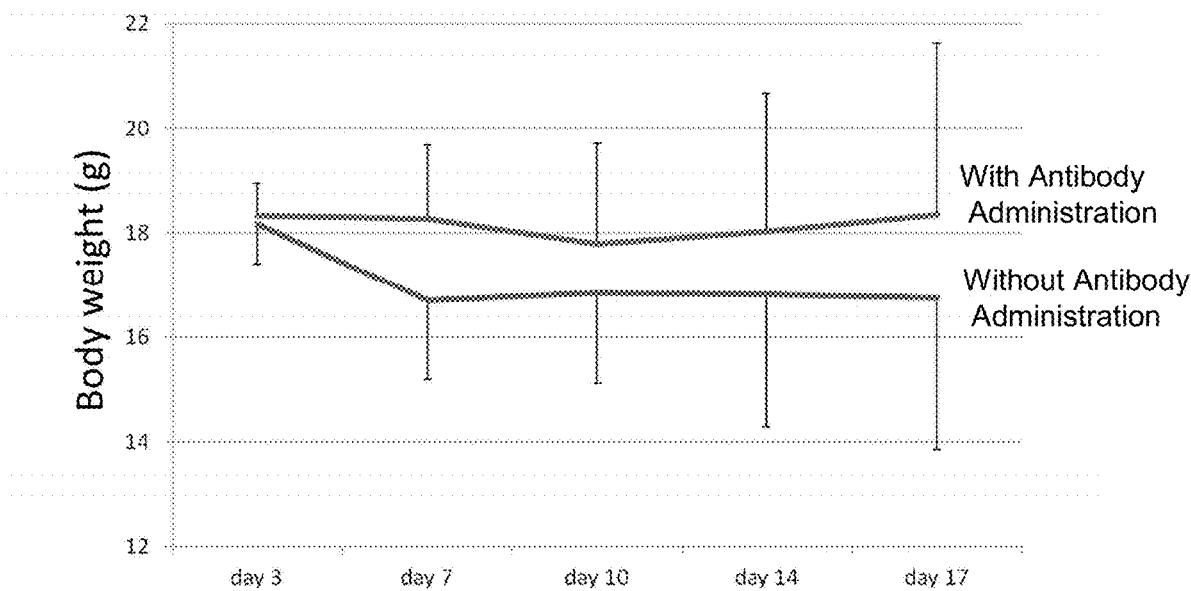
FIG. 20 is a graph illustrating the results of determining a time course of body weight changes in pulmonary fibrosis model mice when an anti-integrin α8β1 antibody according to an Example was or was not administered.

In the bleomycin-induced pulmonary fibrosis mice, the degree of fibrosis affects their body weight. The time course of body weight changes of each pulmonary fibrosis mouse was determined (FIG. 20). The results demonstrated that the mice without the #3 antibody administration exhibited an average decrease in body weight of 1.8 g (about 10%) from Day 3 to Day 7 after the bleomycin administration. By contrast, the mice with the #3 antibody administration exhibited almost no decrease in body weight. That is, the #3 antibody administration seems to suppress a body weight reduction due to fibrosis.

(4) Measuring Levels of Col α1 (I) and α-SMA Gene Expressions

A quantitative PCR method was used to analyze levels of Col α1(I) and α-SMA gene expressions in the lung of each pulmonary fibrosis mouse. Then, the results were compared between the mice with the #3 antibody administration and the mice without antibody administration. FIG. 19 shows relative expression levels when the levels of the mice with the #3 antibody administration were set to 1.

The levels of α-SMA expression in the mice without antibody administration were 4 times or more than those in the mice with the #3 antibody administration. The levels of Col α1(I) expression were 8 times or more. The #3 antibody administration reduced the levels of expression of fibrosis-related genes in the lung of each bleomycin-induced model mouse.

(5) Quantification of Hydroxyproline

Figure 21:
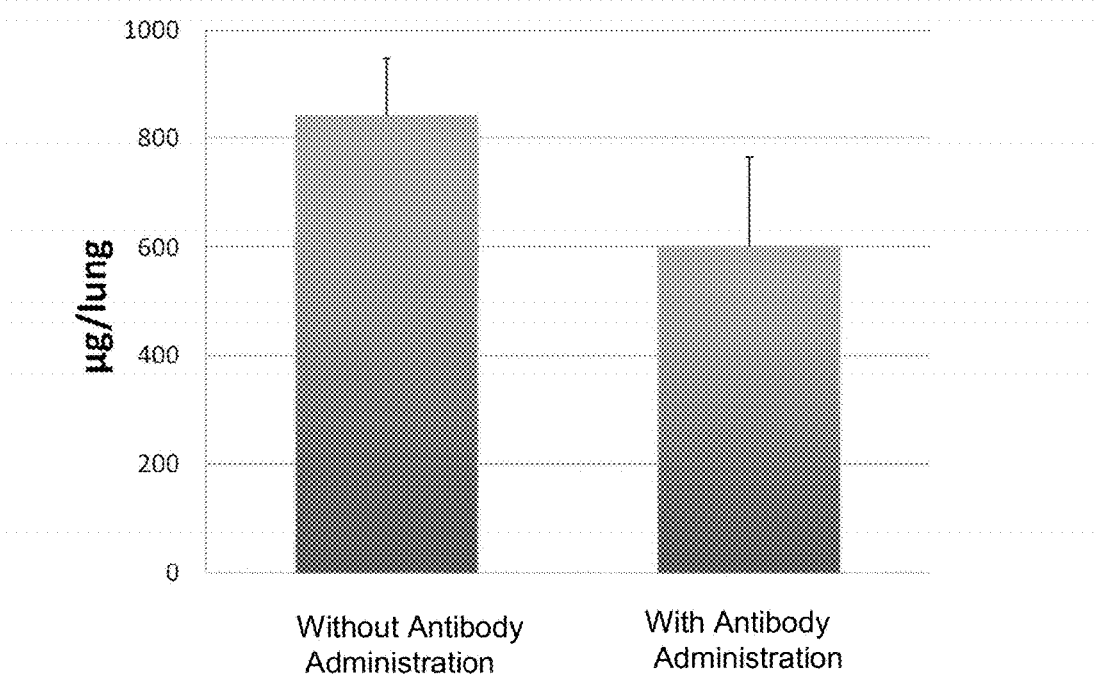
FIG. 21 is a graph illustrating the results of measuring hydroxyproline content in the lungs of pulmonary fibrosis model mice when an anti-integrin α8β1 antibody according to an Example was or was not administered.

The hydroxyproline content in the lung of each pulmonary fibrosis mouse was compared between the mice with the #3 antibody administration and the mice without antibody administration. FIG. 21 shows the results. The #3 antibody administration reduced the content of hydroxyproline in the pulmonary fibrosis mice from 840.7 ng/g pulmonary tissue to 602.8 ng/g pulmonary tissue.

<Example 8> Evaluation of Blocking Activity of #5 and #26 Antibodies Toward Integrin α8β1

First, nephronectin (2.5 mg/ml) was immobilized on a 96-well plate. Next, K562 cells forced to express α8β1 were treated with different concentrations (0.05 to 5 ng/ml) of the #3, #5, and #26 antibodies. Then, the treated cells were added at 1×10 E5 cells/well to the above plate. After the cells were cultured for 1 hour, the adherent cells were stained and their absorbance was measured.

Figure 22:
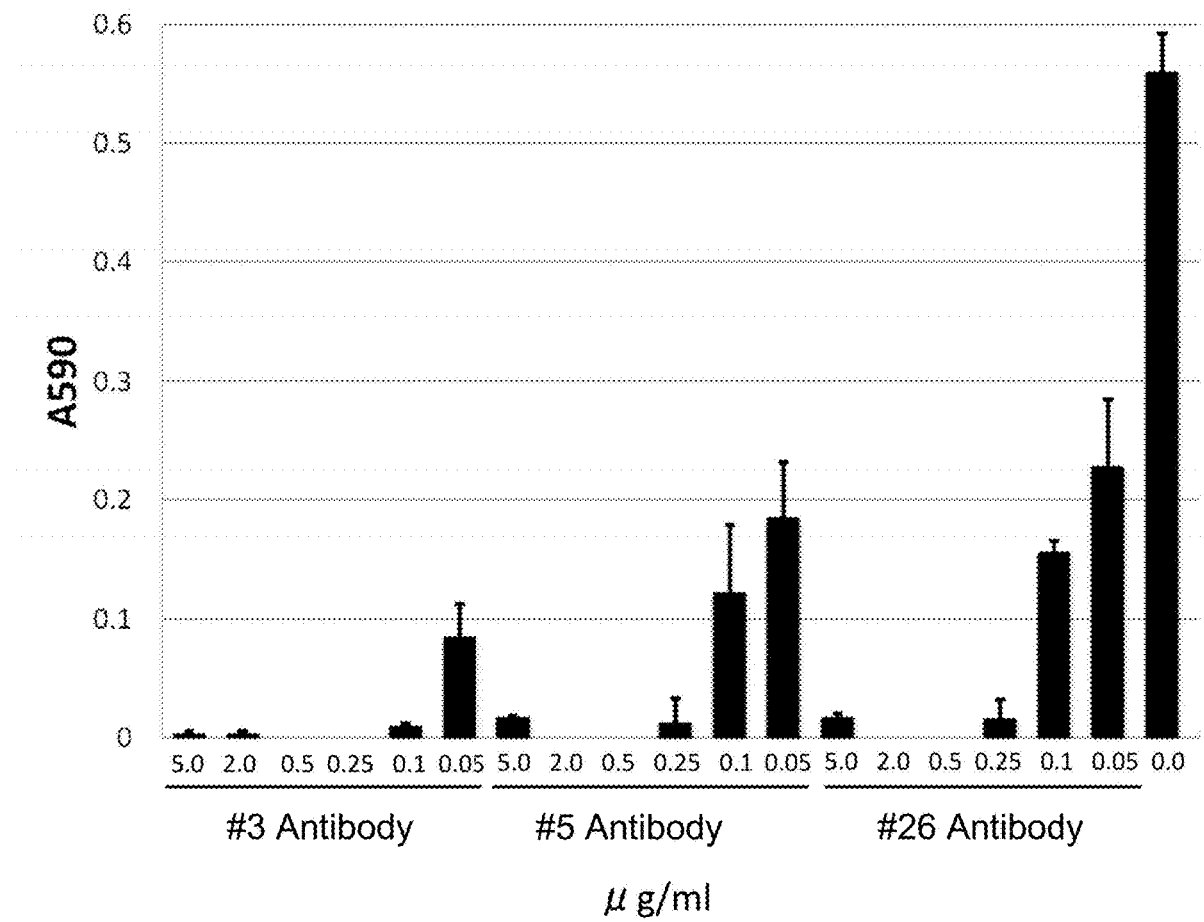
FIG. 22 shows the results of measuring the integrin α8β1-blocking activity of an anti-integrin α8β1 antibody according to an Example.

The results demonstrated that the #3, #5, and #26 antibodies blocked the binding between the α8β1-expressing K562 cells and nephronectin (FIG. 22). These results also indicate that the #3, #5, and #26 antibodies function as an antagonist for integrin α8β1. In addition, it is conceivable that the #5 and #26 antibodies, like the #3 antibody, are characterized by suppressing fibrosis.

<Example 9> Evaluation of Cross-Reactivity of #5 and #26 Antibodies

Figure 23:
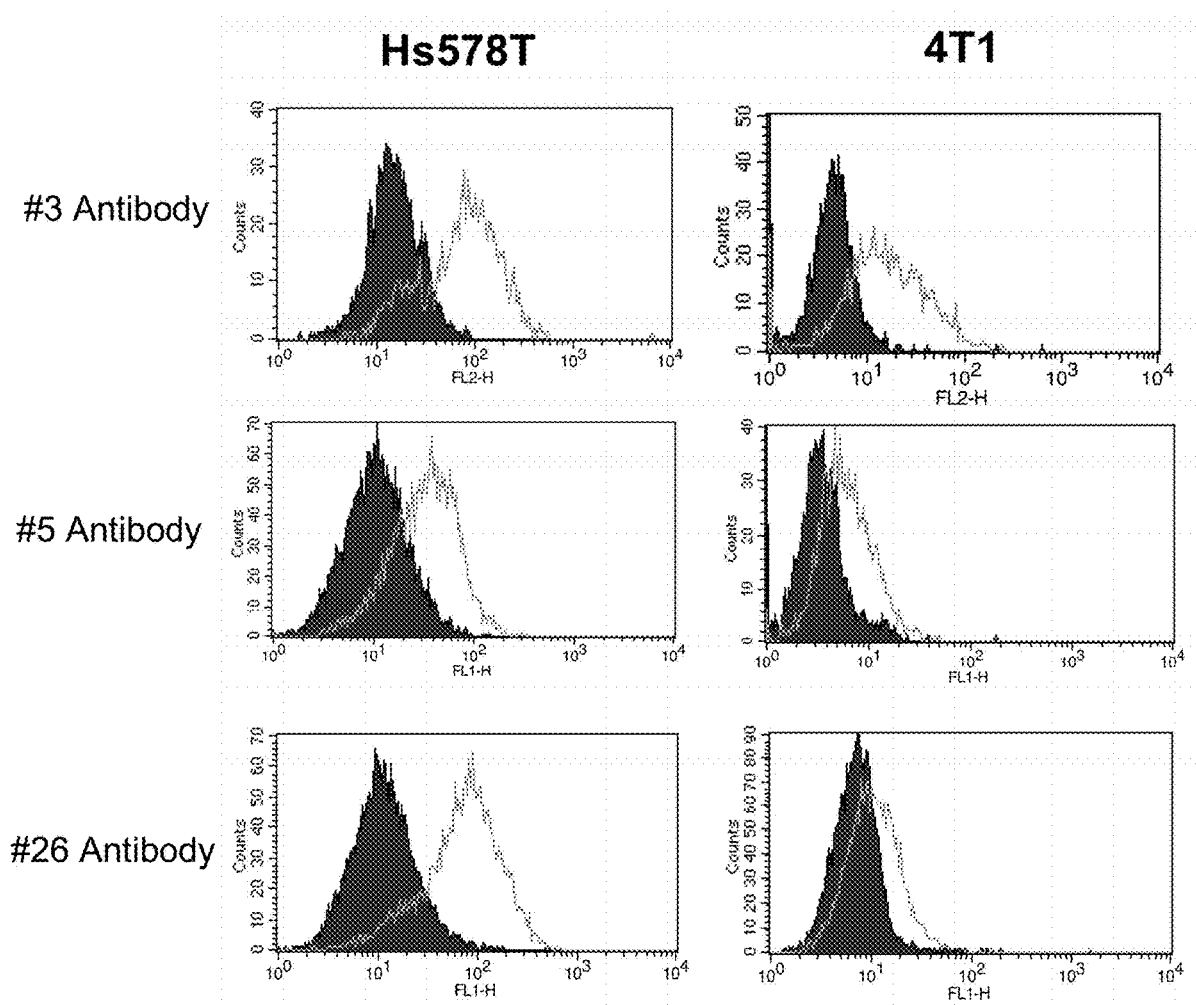
FIG. 23 shows the results of FACS analysis of anti-integrin α8β1 antibodies according to Examples regarding cross-reactivity to integrins α8β1 derived from a human and a mouse.

Integrin α8β1-expressing human- and mouse-derived breast cancer cell lines (Hs578T and 4T1, respectively) were used to examine cross-reactivity of the #3, #5, and #26 antibodies by FACS analysis. The results showed that when any of the human- and mouse-derived cells was used and the #3, #5, and #26 antibodies were each reacted with the cells, a peak position was clearly shifted in the right direction compared with that when no antibody was reacted (FIG. 23). This demonstrates that the #5 and #26 antibodies can bind to integrins α8β1 derived from both a human and a mouse.

<Example 10> Evaluation of Epitope of #5 Antibody

Figure 24:
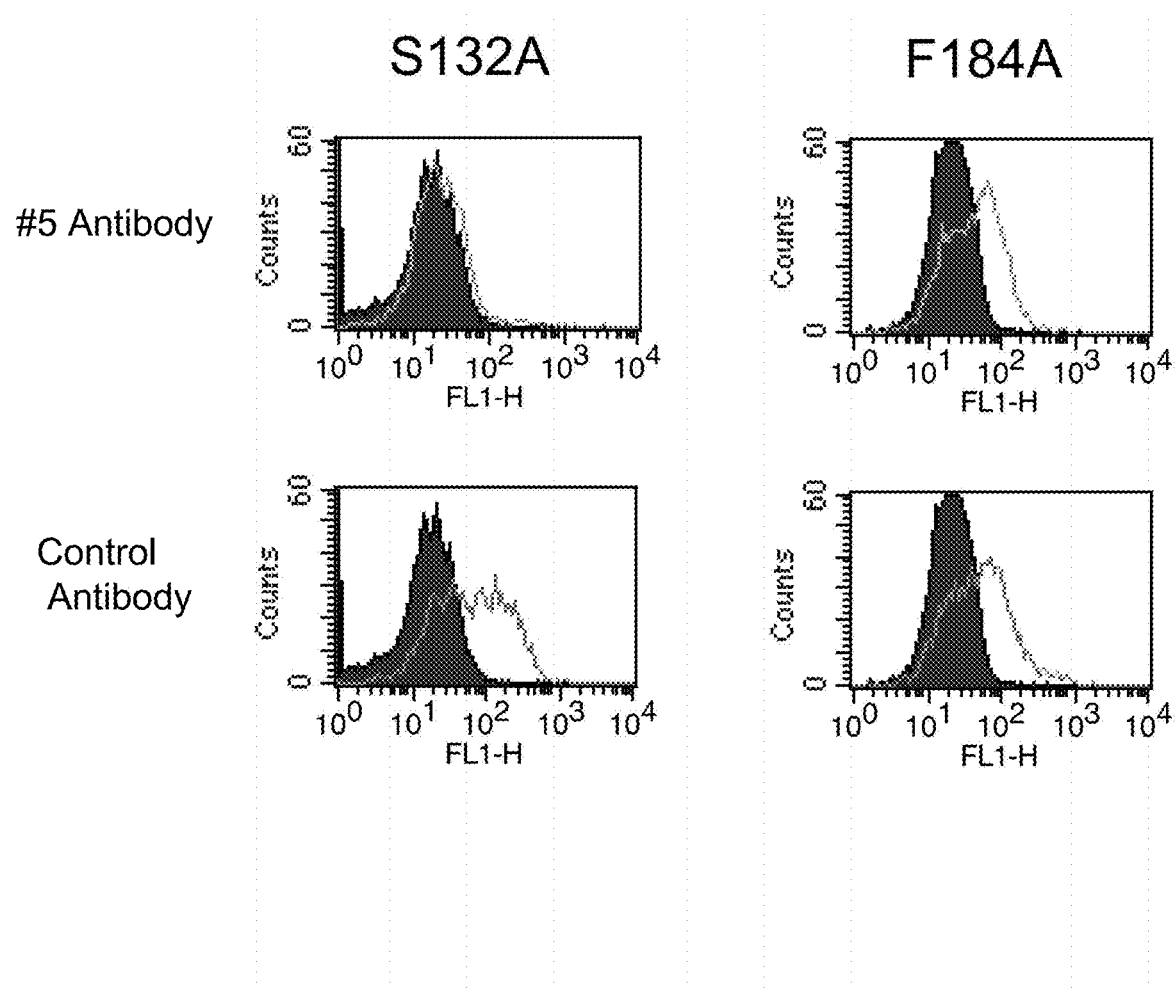
FIG. 24 shows the results of FACS analysis when cells expressing the integrin α8β1 S132 mutant (a stable cell line) were reacted with an anti-integrin α8β1 antibody according to an Example or with a control anti-α8 antibody.

The α8β1-inhibitory #5 antibody, like the #3 antibody, was generated using a chicken as a host. Accordingly, the #5 antibody should recognize a sequence of the human α8 chain, which sequence is different from that of the chicken α8 chain. Next, amino acids in the sequence of the human α8 chain, which amino acids are different from those of the chicken α8 chain, were mutated to create a total of 22 human-α8-chain-mutant cDNAs. Each of these human α8 chain mutants was transiently expressed in CHO cells, and the cells were reacted with the #5 antibody. The #5 antibody failed to react with the S132 mutant, but still reacted with the wild type and the other 21 mutants. Then, in order to exclude the possibility that the S132 mutant was insufficiently expressed due to its transient expression, a stable cell line was established and the antibody was likewise reacted with the mutant. The antibody, however, still did not react therewith. Meanwhile, the S132 mutant well reacted with a control anti-α8 antibody. This result verified that the S132 mutant was sufficiently expressed (FIG. 24). This control anti-α8 antibody recognizes a site other than the mutated positions of the above 22 mutants. The above results indicate that an epitope recognized by the #5 antibody is localized to S132 and a periphery thereof.

The S132, which was recognized by the #5 antibody, and R120, which was recognized by the #3 antibody, of the α chain are each localized to a cap subdomain of the α chain. Hence, it is suggested that when an antibody inhibits the binding between integrin α8β1 and osteopontin, it is critical for the antibody to recognize an amino acid in the cap subdomain.

The above results of Examples 1 to 10 demonstrate that use of an antagonist for integrin α8β1 can suppress fibrosis. In addition, use of an anti-integrin α8β1 antibody that specifically recognizes R120 of the integrin α8 chain and a periphery thereof or S132 and a periphery thereof can suppress fibrosis.

Hereinabove, the present invention has been described based on the Examples. These Examples are absolutely examples. It should be understood by those skilled in the art that various modifications are allowed, and those modifications are also within the scope of the present invention.

The invention claimed is:

1. A method of treating fibrosis comprising administering to a subject an anti-integrin α8β1 monoclonal antibody, wherein the fibrosis occurs in the kidney, and the anti-integrin α8β1 monoclonal antibody is selected from the group consisting of:
   a) an anti-integrin α8β1 monoclonal antibody comprising: heavy chain CDR1 having the amino acid sequence set forth in SEQ ID No: 1; heavy chain CDR2 having the amino acid sequence set forth in SEQ ID No: 2; heavy chain CDR3 having the amino acid sequence set forth in SEQ ID No: 3; light chain CDR1 having the amino acid sequence set forth in SEQ ID No: 4; light chain CDR2 having the amino acid sequence set forth in SEQ ID No: 5; and light chain CDR3 having the amino acid sequence set forth in SEQ ID No: 6;
   b) an anti-integrin α8β1 monoclonal antibody comprising: heavy chain CDR1 having the amino acid sequence set forth in SEQ ID No: 10; heavy chain CDR2 having the amino acid sequence set forth in SEQ ID No: 11; heavy chain CDR3 having the amino acid sequence set forth in SEQ ID No: 12; light chain CDR1 having the amino acid sequence set forth in SEQ ID No: 13; light chain CDR2 having the amino acid sequence set forth in SEQ ID No: 14; and light chain CDR3 having the amino acid sequence set forth in SEQ ID No: 15;

c) an anti-integrin α8β1 monoclonal antibody comprising: heavy chain CDR1 having the amino acid sequence set forth in SEQ ID No: 16; heavy chain CDR2 having the amino acid sequence set forth in SEQ ID No: 17; heavy chain CDR3 having the amino acid sequence set forth in SEQ ID No: 18; light chain CDR1 having the amino acid sequence set forth in SEQ ID No: 19; light chain CDR2 having the amino acid sequence set forth in SEQ ID No: 20; and light chain CDR3 having the amino acid sequence set forth in SEQ ID No: 21.

2. The method of claim 1, wherein the anti-integrin α8β1 monoclonal antibody binds to integrin α8 expressed on the surface of a cell.

3. The method of claim 2, wherein the integrin α8 is of the sequence of SEQ ID NO:7.

4. The method of claim 2, wherein the anti-integrin α8β1 monoclonal antibody inhibits binding of integrin α8β1 to its ligand.

5. The method of claim 3, wherein the anti-integrin α8β1 monoclonal antibody inhibits binding of integrin α8β1 to its ligand.

6. The method of claim 4, wherein the anti-integrin α8β1 monoclonal antibody is an anti-integrin α8β1 monoclonal antibody that does not bind to a R120K mutant or a S132A mutant of the integrin α8 chain having signal peptide, or a R82K mutant or a S94A mutant of the integrin α8 chain without signal peptide, while binding to a wild type integrin α8 chain.

7. The method of claim 1, wherein the anti-integrin α8β1 monoclonal antibody specifically binds to R120 of the integrin α8 chain of SEQ ID NO:7 having signal peptide and a periphery thereof, S132 of the integrin α8 chain of SEQ ID NO:7 having signal peptide and a periphery thereof, R82 of the integrin α8 chain of SEQ ID NO:7 without signal peptide and a periphery thereof, or S94 of the integrin α8 chain of SEQ ID NO:7 without signal peptide and a periphery thereof, and inhibits binding of integrin α8β1 to its ligand, wherein said integrin α8 chain of SEQ ID NO:7 to which said antibody binds is expressed on the surface of a cell, wherein the R120 of the integrin α8 chain of SEQ ID NO:7 having signal peptide and a periphery thereof are amino acid sequence of positions 114, 115, 116, 117, 118, 119, 120, 121, 122, 123, 124, 125, and 126 of the integrin α8 chain, the S132 of the integrin α8 chain of SEQ ID NO:7 having signal peptide and a periphery thereof are amino acid sequence of positions 126, 127, 128, 129, 130, 131, 132, 133, 134, 135, 136, 137, and 138 of the integrin α8 chain, the R82 of the integrin α8 chain of SEQ ID NO:7 without signal peptide and a periphery thereof are amino acid sequence of positions 76, 77, 78, 79, 80, 81, 82, 83, 84, 85, 86, 87, and 88 of the integrin α8 chain, and the S94 of the integrin α8 chain of SEQ ID NO:7 without signal peptide and a periphery thereof are amino acid sequence of positions 88, 89, 90, 91, 92, 93, 94, 95, 96, 97, 98, 99, and 100 of the integrin α8 chain.

8. The method of treating fibrosis according to claim 1, wherein the anti-integrin α8β1 monoclonal antibody is an anti-integrin α8β1 monoclonal antibody capable of binding to any of integrins α8β1 derived from a human, mouse, and rat.

9. The method of treating fibrosis according to claim 1, wherein the anti-integrin α8β1 monoclonal antibody is an antigen-binding fragment.

10. The method of treating fibrosis according to claim 4, wherein the ligand is at least one ligand selected from the group consisting of osteopontin, fibronectin, vitronectin, and tenascin.

11. A method of treating a disease accompanied by progression of fibrosis occurred in the kidney, comprising administering to a subject an anti-integrin α8β1 monoclonal antibody that is selected from the group consisting of:

a) an anti-integrin α8β1 monoclonal antibody comprising: heavy chain CDR1 having the amino acid sequence set forth in SEQ ID No: 1; heavy chain CDR2 having the amino acid sequence set forth in SEQ ID No: 2; heavy chain CDR3 having the amino acid sequence set forth in SEQ ID No: 3; light chain CDR1 having the amino acid sequence set forth in SEQ ID No: 4; light chain CDR2 having the amino acid sequence set forth in SEQ ID No: 5; and light chain CDR3 having the amino acid sequence set forth in SEQ ID No: 6;

b) an anti-integrin α8β1 monoclonal antibody comprising: heavy chain CDR1 having the amino acid sequence set forth in SEQ ID No: 10; heavy chain CDR2 having the amino acid sequence set forth in SEQ ID No: 11; heavy chain CDR3 having the amino acid sequence set forth in SEQ ID No: 12; light chain CDR1 having the amino acid sequence set forth in SEQ ID No: 13; light chain CDR2 having the amino acid sequence set forth in SEQ ID No: 14; and light chain CDR3 having the amino acid sequence set forth in SEQ ID No: 15;

c) an anti-integrin α8β1 monoclonal antibody comprising: heavy chain CDR1 having the amino acid sequence set forth in SEQ ID No: 16; heavy chain CDR2 having the amino acid sequence set forth in SEQ ID No: 17; heavy chain CDR3 having the amino acid sequence set forth in SEQ ID No: 18; light chain CDR1 having the amino acid sequence set forth in SEQ ID No: 19; light chain CDR2 having the amino acid sequence set forth in SEQ ID No: 20; and light chain CDR3 having the amino acid sequence set forth in SEQ ID No: 21.

12. A method of suppressing weight reduction caused by fibrosis occurred in the kidney, comprising administering to a subject an anti-integrin α8β1 monoclonal antibody that is selected from the group consisting of:

a) an anti-integrin α8β1 monoclonal antibody comprising: heavy chain CDR1 having the amino acid sequence set forth in SEQ ID No: 1; heavy chain CDR2 having the amino acid sequence set forth in SEQ ID No: 2; heavy chain CDR3 having the amino acid sequence set forth in SEQ ID No: 3; light chain CDR1 having the amino acid sequence set forth in SEQ ID No: 4; light chain CDR2 having the amino acid sequence set forth in SEQ ID No: 5; and light chain CDR3 having the amino acid sequence set forth in SEQ ID No: 6;

b) an anti-integrin α8β1 monoclonal antibody comprising: heavy chain CDR1 having the amino acid sequence set forth in SEQ ID No: 10; heavy chain CDR2 having the amino acid sequence set forth in SEQ ID No: 11; heavy chain CDR3 having the amino acid sequence set forth in SEQ ID No: 12; light chain CDR1 having the amino acid sequence set forth in SEQ ID No: 13; light chain CDR2 having the amino acid sequence set forth in SEQ ID No: 14; and light chain CDR3 having the amino acid sequence set forth in SEQ ID No: 15;

c) an anti-integrin α8β1 monoclonal antibody comprising: heavy chain CDR1 having the amino acid sequence set forth in SEQ ID No: 16; heavy chain CDR2 having the amino acid sequence set forth in SEQ ID No: 17; heavy chain CDR3 having the amino acid sequence set forth in SEQ ID No: 18; light chain CDR1 having the amino acid sequence set forth in SEQ ID No: 19; light chain CDR2 having the amino acid sequence set forth in SEQ ID No: 20; and light chain CDR3 having the amino acid sequence set forth in SEQ ID No: 21.

13. The method of claim 1, wherein the anti-integrin α8β1 monoclonal antibody specifically binds to R120 of the integrin α8 chain of SEQ ID NO:7 having signal peptide, S132 of the integrin α8 chain of SEQ ID NO:7 having signal peptide, R82 of the integrin α8 chain of SEQ ID NO:7 without signal peptide, or S94 of the integrin α8 chain of SEQ ID NO:7 without signal peptide, and inhibits binding of integrin α8β1 to its ligand, wherein the amino acid to which the antibody specifically binds is comprised within an epitope comprising sequences of SEQ ID NO:7.

14. The method of claim 1, wherein the administering of the anti-integrin α8β1 monoclonal antibody is the sole approach used to treat the subject.

15. The method of treating fibrosis according to claim 1, wherein the anti-integrin α8β1 monoclonal antibody suppresses an increase in levels of expression of collagen α1(I) or smooth muscle actin genes, or in hydroxyproline content in the subject.

16. The method of claim 1, wherein the anti-integrin α8β1 monoclonal antibody is the sole therapy administered to the subject to treat the fibrosis.

* * * * *

SEQUENCE LISTING

```
<160> NUMBER OF SEQ ID NOS: 32

<210> SEQ ID NO 1
<211> LENGTH: 5
<212> TYPE: PRT
<213> ORGANISM: Gallus gallus

<400> SEQUENCE: 1

Ser Tyr Asp Met Val
1               5

<210> SEQ ID NO 2
<211> LENGTH: 16
<212> TYPE: PRT
<213> ORGANISM: Gallus gallus

<400> SEQUENCE: 2

Ile Tyr Ser Ala Gly Ser Gly Pro Gln Tyr Ala Pro Ala Val Lys Gly
1               5                   10                  15

<210> SEQ ID NO 3
<211> LENGTH: 18
<212> TYPE: PRT
<213> ORGANISM: Gallus gallus

<400> SEQUENCE: 3

Ala Asp Ser Thr Tyr Cys Ala Ser Gly Ser Cys Tyr Ala Ala Asp Ser
1               5                   10                  15

Ile Asp

<210> SEQ ID NO 4
<211> LENGTH: 8
<212> TYPE: PRT
<213> ORGANISM: Gallus gallus

<400> SEQUENCE: 4

Ser Gly Gly Gly Ser Trp Tyr Gly
1               5

<210> SEQ ID NO 5
<211> LENGTH: 7
<212> TYPE: PRT
<213> ORGANISM: Gallus gallus

<400> SEQUENCE: 5

Asp Asn Thr Asn Arg Pro Ser
1               5

<210> SEQ ID NO 6
<211> LENGTH: 9
<212> TYPE: PRT
<213> ORGANISM: Gallus gallus
```

<400> SEQUENCE: 6

Gly Ser Ala Asp Ser Thr Asp Ala Val
1               5

<210> SEQ ID NO 7
<211> LENGTH: 1063
<212> TYPE: PRT
<213> ORGANISM: Homo sapiens

<400> SEQUENCE: 7

Met Ser Pro Gly Ala Ser Arg Gly Pro Arg Gly Ser Gln Ala Pro Leu
1               5                   10                  15

Ile Ala Pro Leu Cys Cys Ala Ala Ala Leu Gly Met Leu Leu Trp
            20                  25                  30

Ser Pro Ala Cys Gln Ala Phe Asn Leu Asp Val Glu Lys Leu Thr Val
            35                  40                  45

Tyr Ser Gly Pro Lys Gly Ser Tyr Phe Gly Tyr Ala Val Asp Phe His
    50                  55                  60

Ile Pro Asp Ala Arg Thr Ala Ser Val Leu Val Gly Ala Pro Lys Ala
65                  70                  75                  80

Asn Thr Ser Gln Pro Asp Ile Val Glu Gly Gly Ala Val Tyr Tyr Cys
                85                  90                  95

Pro Trp Pro Ala Glu Gly Ser Ala Gln Cys Arg Gln Ile Pro Phe Asp
            100                 105                 110

Thr Thr Asn Asn Arg Lys Ile Arg Val Asn Gly Thr Lys Glu Pro Ile
        115                 120                 125

Glu Phe Lys Ser Asn Gln Trp Phe Gly Ala Thr Val Lys Ala His Lys
    130                 135                 140

Gly Lys Val Val Ala Cys Ala Pro Leu Tyr His Trp Arg Thr Leu Lys
145                 150                 155                 160

Pro Thr Pro Glu Lys Asp Pro Val Gly Thr Cys Tyr Val Ala Ile Gln
                165                 170                 175

Asn Phe Ser Ala Tyr Ala Glu Phe Ser Pro Cys Arg Asn Ser Asn Ala
            180                 185                 190

Asp Pro Glu Gly Gln Gly Tyr Cys Gln Ala Gly Phe Ser Leu Asp Phe
        195                 200                 205

Tyr Lys Asn Gly Asp Leu Ile Val Gly Pro Gly Ser Phe Tyr Trp
    210                 215                 220

Gln Gly Gln Val Ile Thr Ala Ser Val Ala Asp Ile Ile Ala Asn Tyr
225                 230                 235                 240

Ser Phe Lys Asp Ile Leu Arg Lys Leu Ala Gly Glu Lys Gln Thr Glu
                245                 250                 255

Val Ala Pro Ala Ser Tyr Asp Asp Ser Tyr Leu Gly Tyr Ser Val Ala
            260                 265                 270

Ala Gly Glu Phe Thr Gly Asp Ser Gln Gln Glu Leu Val Ala Gly Ile
        275                 280                 285

Pro Arg Gly Ala Gln Asn Phe Gly Tyr Val Ser Ile Ile Asn Ser Thr
    290                 295                 300

Asp Met Thr Phe Ile Gln Asn Phe Thr Gly Glu Gln Met Ala Ser Tyr
305                 310                 315                 320

Phe Gly Tyr Thr Val Val Ser Asp Val Asn Ser Asp Gly Leu Asp
                325                 330                 335

Asp Val Leu Val Gly Ala Pro Leu Phe Met Glu Arg Glu Phe Glu Ser
            340                 345                 350

-continued

```
Asn Pro Arg Glu Val Gly Gln Ile Tyr Leu Tyr Leu Gln Val Ser Ser
        355                 360                 365

Leu Leu Phe Arg Asp Pro Gln Ile Leu Thr Gly Thr Glu Thr Phe Gly
    370                 375                 380

Arg Phe Gly Ser Ala Met Ala His Leu Gly Asp Leu Asn Gln Asp Gly
385                 390                 395                 400

Tyr Asn Asp Ile Ala Ile Gly Val Pro Phe Ala Gly Lys Asp Gln Arg
                405                 410                 415

Gly Lys Val Leu Ile Tyr Asn Gly Asn Lys Asp Gly Leu Asn Thr Lys
                420                 425                 430

Pro Ser Gln Val Leu Gln Gly Val Trp Ala Ser His Ala Val Pro Ser
            435                 440                 445

Gly Phe Gly Phe Thr Leu Arg Gly Asp Ser Asp Ile Asp Lys Asn Asp
    450                 455                 460

Tyr Pro Asp Leu Ile Val Gly Ala Phe Gly Thr Gly Lys Val Ala Val
465                 470                 475                 480

Tyr Arg Ala Arg Pro Val Val Thr Val Asp Ala Gln Leu Leu Leu His
                485                 490                 495

Pro Met Ile Ile Asn Leu Glu Asn Lys Thr Cys Gln Val Pro Asp Ser
            500                 505                 510

Met Thr Ser Ala Ala Cys Phe Ser Leu Arg Val Cys Ala Ser Val Thr
    515                 520                 525

Gly Gln Ser Ile Ala Asn Thr Ile Val Leu Met Ala Glu Val Gln Leu
    530                 535                 540

Asp Ser Leu Lys Gln Lys Gly Ala Ile Lys Arg Thr Leu Phe Leu Asp
545                 550                 555                 560

Asn His Gln Ala His Arg Val Phe Pro Leu Val Ile Lys Arg Gln Lys
                565                 570                 575

Ser His Gln Cys Gln Asp Phe Ile Val Tyr Leu Arg Asp Glu Thr Glu
            580                 585                 590

Phe Arg Asp Lys Leu Ser Pro Ile Asn Ile Ser Leu Asn Tyr Ser Leu
    595                 600                 605

Asp Glu Ser Thr Phe Lys Glu Gly Leu Glu Val Lys Pro Ile Leu Asn
    610                 615                 620

Tyr Tyr Arg Glu Asn Ile Val Ser Glu Gln Ala His Ile Leu Val Asp
625                 630                 635                 640

Cys Gly Glu Asp Asn Leu Cys Val Pro Asp Leu Lys Leu Ser Ala Arg
                645                 650                 655

Pro Asp Lys His Gln Val Ile Ile Gly Asp Glu Asn His Leu Met Leu
            660                 665                 670

Ile Ile Asn Ala Arg Asn Glu Gly Glu Gly Ala Tyr Glu Ala Glu Leu
    675                 680                 685

Phe Val Met Ile Pro Glu Glu Ala Asp Tyr Val Gly Ile Glu Arg Asn
    690                 695                 700

Asn Lys Gly Phe Arg Pro Leu Ser Cys Glu Tyr Lys Met Glu Asn Val
705                 710                 715                 720

Thr Arg Met Val Val Cys Asp Leu Gly Asn Pro Met Val Ser Gly Thr
                725                 730                 735

Asn Tyr Ser Leu Gly Leu Arg Phe Ala Val Pro Arg Leu Glu Lys Thr
            740                 745                 750

Asn Met Ser Ile Asn Phe Asp Leu Gln Ile Arg Ser Ser Asn Lys Asp
    755                 760                 765

Asn Pro Asp Ser Asn Phe Val Ser Leu Gln Ile Asn Ile Thr Ala Val
```

```
            770                 775                 780
Ala Gln Val Glu Ile Arg Gly Val Ser His Pro Pro Gln Ile Val Leu
785                 790                 795                 800

Pro Ile His Asn Trp Glu Pro Glu Glu Pro His Lys Glu Glu Glu
                805                 810                 815

Val Gly Pro Leu Val Glu His Ile Tyr Glu Leu His Asn Ile Gly Pro
                820                 825                 830

Ser Thr Ile Ser Asp Thr Ile Leu Glu Val Gly Trp Pro Phe Ser Ala
                835                 840                 845

Arg Asp Glu Phe Leu Leu Tyr Ile Phe His Ile Gln Thr Leu Gly Pro
            850                 855                 860

Leu Gln Cys Gln Pro Asn Pro Asn Ile Asn Pro Gln Asp Ile Lys Pro
865                 870                 875                 880

Ala Ala Ser Pro Glu Asp Thr Pro Glu Leu Ser Ala Phe Leu Arg Asn
                885                 890                 895

Ser Thr Ile Pro His Leu Val Arg Lys Arg Asp Val His Val Val Glu
                900                 905                 910

Phe His Arg Gln Ser Pro Ala Lys Ile Leu Asn Cys Thr Asn Ile Glu
            915                 920                 925

Cys Leu Gln Ile Ser Cys Ala Val Gly Arg Leu Glu Gly Gly Glu Ser
    930                 935                 940

Ala Val Leu Lys Val Arg Ser Arg Leu Trp Ala His Thr Phe Leu Gln
945                 950                 955                 960

Arg Lys Asn Asp Pro Tyr Ala Leu Ala Ser Leu Val Ser Phe Glu Val
                965                 970                 975

Lys Lys Met Pro Tyr Thr Asp Gln Pro Ala Lys Leu Pro Glu Gly Ser
                980                 985                 990

Ile Val Ile Lys Thr Ser Val Ile Trp Ala Thr Pro Asn Val Ser Phe
            995                 1000                1005

Ser Ile Pro Leu Trp Val Ile Leu Ala Ile Leu Leu Gly Leu
    1010                1015                1020

Leu Val Leu Ala Ile Leu Thr Leu Ala Leu Trp Lys Cys Gly Phe
    1025                1030                1035

Phe Asp Arg Ala Arg Pro Pro Gln Glu Asp Met Thr Asp Arg Glu
    1040                1045                1050

Gln Leu Thr Asn Asp Lys Thr Pro Glu Ala
    1055                1060

<210> SEQ ID NO 8
<211> LENGTH: 798
<212> TYPE: PRT
<213> ORGANISM: Homo sapiens

<400> SEQUENCE: 8

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
                20                  25                  30

Lys Ser Cys Gly Glu Cys Ile Gln Ala Gly Pro Asn Cys Gly Trp Cys
            35                  40                  45

Thr Asn Ser Thr Phe Leu Gln Glu Gly Met Pro Thr Ser Ala Arg Cys
        50                  55                  60

Asp Asp Leu Glu Ala Leu Lys Lys Lys Gly Cys Pro Pro Asp Asp Ile
65                  70                  75                  80
```

```
Glu Asn Pro Arg Gly Ser Lys Asp Ile Lys Lys Asn Lys Asn Val Thr
                85                  90                  95
Asn Arg Ser Lys Gly Thr Ala Glu Lys Leu Lys Pro Glu Asp Ile Thr
            100                 105                 110
Gln Ile Gln Pro Gln Gln Leu Val Leu Arg Leu Arg Ser Gly Glu Pro
        115                 120                 125
Gln Thr Phe Thr Leu Lys Phe Lys Arg Ala Glu Asp Tyr Pro Ile Asp
    130                 135                 140
Leu Tyr Tyr Leu Met Asp Leu Ser Tyr Ser Met Lys Asp Asp Leu Glu
145                 150                 155                 160
Asn Val Lys Ser Leu Gly Thr Asp Leu Met Asn Glu Met Arg Arg Ile
                165                 170                 175
Thr Ser Asp Phe Arg Ile Gly Phe Gly Ser Phe Val Glu Lys Thr Val
            180                 185                 190
Met Pro Tyr Ile Ser Thr Thr Pro Ala Lys Leu Arg Asn Pro Cys Thr
        195                 200                 205
Ser Glu Gln Asn Cys Thr Ser Pro Phe Ser Tyr Lys Asn Val Leu Ser
    210                 215                 220
Leu Thr Asn Lys Gly Glu Val Phe Asn Glu Leu Val Gly Lys Gln Arg
225                 230                 235                 240
Ile Ser Gly Asn Leu Asp Ser Pro Glu Gly Gly Phe Asp Ala Ile Met
                245                 250                 255
Gln Val Ala Val Cys Gly Ser Leu Ile Gly Trp Arg Asn Val Thr Arg
            260                 265                 270
Leu Leu Val Phe Ser Thr Asp Ala Gly Phe His Phe Ala Gly Asp Gly
        275                 280                 285
Lys Leu Gly Gly Ile Val Leu Pro Asn Asp Gly Gln Cys His Leu Glu
    290                 295                 300
Asn Asn Met Tyr Thr Met Ser His Tyr Tyr Asp Tyr Pro Ser Ile Ala
305                 310                 315                 320
His Leu Val Gln Lys Leu Ser Glu Asn Asn Ile Gln Thr Ile Phe Ala
                325                 330                 335
Val Thr Glu Glu Phe Gln Pro Val Tyr Lys Glu Leu Lys Asn Leu Ile
            340                 345                 350
Pro Lys Ser Ala Val Gly Thr Leu Ser Ala Asn Ser Ser Asn Val Ile
        355                 360                 365
Gln Leu Ile Ile Asp Ala Tyr Asn Ser Leu Ser Ser Glu Val Ile Leu
    370                 375                 380
Glu Asn Gly Lys Leu Ser Glu Gly Val Thr Ile Ser Tyr Lys Ser Tyr
385                 390                 395                 400
Cys Lys Asn Gly Val Asn Gly Thr Gly Glu Asn Gly Arg Lys Cys Ser
                405                 410                 415
Asn Ile Ser Ile Gly Asp Glu Val Gln Phe Glu Ile Ser Ile Thr Ser
            420                 425                 430
Asn Lys Cys Pro Lys Lys Asp Ser Asp Ser Phe Lys Ile Arg Pro Leu
        435                 440                 445
Gly Phe Thr Glu Glu Val Glu Val Ile Leu Gln Tyr Ile Cys Glu Cys
    450                 455                 460
Glu Cys Gln Ser Glu Gly Ile Pro Glu Ser Pro Lys Cys His Glu Gly
465                 470                 475                 480
Asn Gly Thr Phe Glu Cys Gly Ala Cys Arg Cys Asn Glu Gly Arg Val
                485                 490                 495
Gly Arg His Cys Glu Cys Ser Thr Asp Glu Val Asn Ser Glu Asp Met
```

```
                500              505              510
Asp Ala Tyr Cys Arg Lys Glu Asn Ser Ser Glu Ile Cys Ser Asn Asn
            515              520              525

Gly Glu Cys Val Cys Gly Gln Cys Val Cys Arg Lys Arg Asp Asn Thr
530              535              540

Asn Glu Ile Tyr Ser Gly Lys Phe Cys Glu Cys Asp Asn Phe Asn Cys
545              550              555              560

Asp Arg Ser Asn Gly Leu Ile Cys Gly Gly Asn Gly Val Cys Lys Cys
            565              570              575

Arg Val Cys Glu Cys Asn Pro Asn Tyr Thr Gly Ser Ala Cys Asp Cys
        580              585              590

Ser Leu Asp Thr Ser Thr Cys Glu Ala Ser Asn Gly Gln Ile Cys Asn
        595              600              605

Gly Arg Gly Ile Cys Glu Cys Gly Val Cys Lys Cys Thr Asp Pro Lys
            610              615              620

Phe Gln Gly Gln Thr Cys Glu Met Cys Gln Thr Cys Leu Gly Val Cys
625              630              635              640

Ala Glu His Lys Glu Cys Val Gln Cys Arg Ala Phe Asn Lys Gly Glu
                645              650              655

Lys Lys Asp Thr Cys Thr Gln Glu Cys Ser Tyr Phe Asn Ile Thr Lys
            660              665              670

Val Glu Ser Arg Asp Lys Leu Pro Gln Pro Val Gln Pro Asp Pro Val
        675              680              685

Ser His Cys Lys Glu Lys Asp Val Asp Asp Cys Trp Phe Tyr Phe Thr
        690              695              700

Tyr Ser Val Asn Gly Asn Asn Glu Val Met Val His Val Val Glu Asn
705              710              715              720

Pro Glu Cys Pro Thr Gly Pro Asp Ile Ile Pro Ile Val Ala Gly Val
                725              730              735

Val Ala Gly Ile Val Leu Ile Gly Leu Ala Leu Leu Leu Ile Trp Lys
            740              745              750

Leu Leu Met Ile Ile His Asp Arg Arg Glu Phe Ala Lys Phe Glu Lys
        755              760              765

Glu Lys Met Asn Ala Lys Trp Asp Thr Gly Glu Asn Pro Ile Tyr Lys
        770              775              780

Ser Ala Val Thr Thr Val Val Asn Pro Lys Tyr Glu Gly Lys
785              790              795

<210> SEQ ID NO 9
<211> LENGTH: 13
<212> TYPE: PRT
<213> ORGANISM: Homo sapiens

<400> SEQUENCE: 9

Thr Asn Asn Arg Lys Ile Arg Val Asn Gly Thr Lys Glu
1               5                   10

<210> SEQ ID NO 10
<211> LENGTH: 5
<212> TYPE: PRT
<213> ORGANISM: Gallus gallus

<400> SEQUENCE: 10

Ser Tyr Asp Met Ala
1               5
```

```
<210> SEQ ID NO 11
<211> LENGTH: 16
<212> TYPE: PRT
<213> ORGANISM: Gallus gallus

<400> SEQUENCE: 11

Ile Asp Asp Asp Ser Phe Thr Leu Tyr Gly Ala Ala Val Lys Gly
1               5                   10                  15

<210> SEQ ID NO 12
<211> LENGTH: 16
<212> TYPE: PRT
<213> ORGANISM: Gallus gallus

<400> SEQUENCE: 12

Val Gly Asp Gly Tyr Cys Gly Trp Ser Ala Cys Gly Gly Ser Ile Asp
1               5                   10                  15

<210> SEQ ID NO 13
<211> LENGTH: 8
<212> TYPE: PRT
<213> ORGANISM: Gallus gallus

<400> SEQUENCE: 13

Ser Gly Asp Glu Ser Tyr Tyr Gly
1               5

<210> SEQ ID NO 14
<211> LENGTH: 7
<212> TYPE: PRT
<213> ORGANISM: Gallus gallus

<400> SEQUENCE: 14

Ser Asn Asp Lys Arg Pro Ser
1               5

<210> SEQ ID NO 15
<211> LENGTH: 11
<212> TYPE: PRT
<213> ORGANISM: Gallus gallus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 15

Gly Xaa Tyr Asp Ser Ser Thr Tyr Ala Gly Ile
1               5                   10

<210> SEQ ID NO 16
<211> LENGTH: 5
<212> TYPE: PRT
<213> ORGANISM: Gallus gallus

<400> SEQUENCE: 16

Gly His Asp Met Ala
1               5

<210> SEQ ID NO 17
<211> LENGTH: 16
<212> TYPE: PRT
<213> ORGANISM: Gallus gallus

<400> SEQUENCE: 17

Ile Gly Ser Ser Gly Ser Asn Thr Asn Tyr Gly Thr Ala Val Lys Gly
1               5                   10                  15
```

```
<210> SEQ ID NO 18
<211> LENGTH: 15
<212> TYPE: PRT
<213> ORGANISM: Gallus gallus

<400> SEQUENCE: 18

Pro Gly Ser Cys Tyr Gly Cys Thr Pro Asp Ala Gly Glu Ile Asp
1               5                  10                  15

<210> SEQ ID NO 19
<211> LENGTH: 9
<212> TYPE: PRT
<213> ORGANISM: Gallus gallus

<400> SEQUENCE: 19

Ser Gly Ser Ser Gly Ser Tyr Tyr Gly
1               5

<210> SEQ ID NO 20
<211> LENGTH: 7
<212> TYPE: PRT
<213> ORGANISM: Gallus gallus

<400> SEQUENCE: 20

Glu Ser Thr Lys Arg Pro Ser
1               5

<210> SEQ ID NO 21
<211> LENGTH: 10
<212> TYPE: PRT
<213> ORGANISM: Gallus gallus

<400> SEQUENCE: 21

Gly Asn Glu Asp Ser Ser Tyr Val Gly Ile
1               5                  10

<210> SEQ ID NO 22
<211> LENGTH: 33
<212> TYPE: PRT
<213> ORGANISM: Bos taurus

<400> SEQUENCE: 22

Gln Ile Pro Phe Asp Asn Thr Asn Arg Lys Ile Arg Val Asn Gly
1               5                  10                  15

Thr Lys Glu Pro Ile Glu Phe Lys Ser Asn Gln Trp Phe Gly Ala Thr
                20                  25                  30

Val

<210> SEQ ID NO 23
<211> LENGTH: 33
<212> TYPE: PRT
<213> ORGANISM: Sus scrofa

<400> SEQUENCE: 23

Gln Ile Pro Phe Asp Asn Thr Asn Arg Lys Ile Arg Val Asn Gly
1               5                  10                  15

Thr Lys Glu Pro Ile Glu Phe Lys Ser Asn Gln Trp Phe Gly Ala Thr
                20                  25                  30

Val

<210> SEQ ID NO 24
```

-continued

```
<211> LENGTH: 33
<212> TYPE: PRT
<213> ORGANISM: Canis familiaris

<400> SEQUENCE: 24

Gln Ile Pro Phe Asp Asn Thr Asn Arg Lys Ile Arg Val Asn Gly
1               5                   10                  15

Thr Lys Glu Pro Ile Glu Phe Lys Ser Asn Gln Trp Phe Gly Ala Thr
            20                  25                  30

Val

<210> SEQ ID NO 25
<211> LENGTH: 33
<212> TYPE: PRT
<213> ORGANISM: Mus musculus

<400> SEQUENCE: 25

Gln Ile Pro Phe Asp Thr Thr Asn Arg Lys Ile Arg Val Asn Gly
1               5                   10                  15

Thr Lys Glu Pro Ile Glu Phe Lys Ser Asn Gln Trp Phe Gly Ala Thr
            20                  25                  30

Val

<210> SEQ ID NO 26
<211> LENGTH: 33
<212> TYPE: PRT
<213> ORGANISM: Rattus rattus

<400> SEQUENCE: 26

Gln Ile Pro Phe Asp Thr Thr Asn Arg Lys Ile Arg Val Asn Gly
1               5                   10                  15

Thr Lys Glu Pro Ile Glu Phe Lys Ser Asn Gln Trp Phe Gly Ala Thr
            20                  25                  30

Val

<210> SEQ ID NO 27
<211> LENGTH: 33
<212> TYPE: PRT
<213> ORGANISM: Mesocricetus auratus

<400> SEQUENCE: 27

Gln Ile Pro Phe Asp Thr Thr Asn Arg Lys Ile Arg Val Asn Gly
1               5                   10                  15

Thr Lys Glu Pro Ile Glu Phe Lys Ser Asn Gln Trp Phe Gly Ala Thr
            20                  25                  30

Val

<210> SEQ ID NO 28
<211> LENGTH: 33
<212> TYPE: PRT
<213> ORGANISM: Pan troglodytes

<400> SEQUENCE: 28

Gln Ile Pro Phe Asp Thr Thr Asn Arg Lys Ile Arg Val Asn Gly
1               5                   10                  15

Thr Lys Glu Pro Ile Glu Phe Lys Ser Asn Gln Trp Phe Gly Ala Thr
            20                  25                  30

Val
```

```
<210> SEQ ID NO 29
<211> LENGTH: 33
<212> TYPE: PRT
<213> ORGANISM: Hylobates lar

<400> SEQUENCE: 29

Gln Ile Pro Phe Asp Thr Thr Asn Asn Arg Lys Ile Arg Val Asn Gly
1               5                   10                  15

Thr Lys Glu Pro Ile Glu Phe Lys Ser Asn Gln Trp Phe Gly Ala Thr
            20                  25                  30

Val

<210> SEQ ID NO 30
<211> LENGTH: 33
<212> TYPE: PRT
<213> ORGANISM: Macaca mulatta

<400> SEQUENCE: 30

Gln Ile Pro Phe Asp Thr Thr Asn Asn Arg Lys Ile Arg Val Asn Gly
1               5                   10                  15

Thr Lys Glu His Ile Glu Phe Lys Ser Asn Gln Trp Phe Gly Ala Thr
            20                  25                  30

Val

<210> SEQ ID NO 31
<211> LENGTH: 33
<212> TYPE: PRT
<213> ORGANISM: Callithrix jacchus

<400> SEQUENCE: 31

Gln Ile Pro Phe Asp Thr Thr Asn Asn Arg Lys Ile Arg Val Asn Gly
1               5                   10                  15

Thr Lys Glu Pro Ile Glu Phe Lys Ser Asn Gln Trp Phe Gly Ala Thr
            20                  25                  30

Val

<210> SEQ ID NO 32
<211> LENGTH: 33
<212> TYPE: PRT
<213> ORGANISM: Homo sapiens

<400> SEQUENCE: 32

Gln Ile Pro Phe Asp Thr Thr Asn Asn Arg Lys Ile Arg Val Asn Gly
1               5                   10                  15

Thr Lys Glu Pro Ile Glu Phe Lys Ser Asn Gln Trp Phe Gly Ala Thr
            20                  25                  30

Val
```